US006600018B1

(12) United States Patent
Rubin et al.

(10) Patent No.: US 6,600,018 B1
(45) Date of Patent: Jul. 29, 2003

(54) SECRETED FRIZZLED RELATED PROTEIN, SFRP, FRAGMENTS AND METHODS OF USE THEREOF

(75) Inventors: Jeffrey S. Rubin, Rockville, MD (US); Susan Cumberledge, Amherst, MA (US); Frieda Reichsman, Amherst, MA (US); Aykut Uren, Baltimore, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/546,043

(22) Filed: Apr. 10, 2000

(51) Int. Cl.$^7$ .................. C07K 14/00; A61K 38/02; A61K 38/17; C07H 21/04
(52) U.S. Cl. .................. 530/350; 530/300; 530/402; 514/2; 435/7.1; 435/69.1; 435/325.1; 435/320.1; 424/192.1; 536/23.1; 536/23.4
(58) Field of Search .................. 530/300, 350, 530/402; 514/2; 435/7.1, 69.1, 325.1, 320.1; 424/192.1; 536/23.1, 23.4

(56) References Cited

U.S. PATENT DOCUMENTS

| 5,851,984 A | 12/1998 | Matthews et al. ............ 514/12 |
| 6,043,053 A | 3/2000 | Barnes et al. ............... 436/69.1 |

FOREIGN PATENT DOCUMENTS

| WO | WO 97/39357 | 10/1997 |
| WO | WO 98/13493 | 4/1998 |
| WO | WO 98/54325 | 12/1998 |
| WO | WO 99/26960 | 6/1999 |

OTHER PUBLICATIONS

Wodraz, A. et al., Mechanism of Wnt signaling in Development, Ann. Rev. Cell Dev. Biol., vol. 14, pp. 59–88, 1998.*
McMahon, A. P., The Wnt Family of Developmental regulators, TIG, vol. *, pp. 236–342, 1992.*
Cadigan, K. M. et al., Wnt Signaling: a Common Theme in Animal Development, Genes and Development., vol. 11, pp. 3286–3305, 1997.*
Nusse, R. et al., Wnt Genes, Cell, vol. 69, pp. 1073–1087, 1992.*
Bafico, *J. Biol. Chem.* 274:16180–16187, 1999.
Finch et al., *Proc. Natl. Acad. Sci. USA* 94:6770–6775, Jun., 1997.
Melkonyan et al., *Proc. Natl. Acad. Sci. USA* 94:13636–13641, 1997.
Rattner et al., *Proc. Natl. Acad. Sci. USA* 94:2859–2863, 1997.
Ugolini, *Oncogene* 18:1903–1910, 1999.
Üren et al., *J. Biol. Chem.* 275: 4374–4382, 2000.
Zhou, *J. Cancer* 78: 95–99, 1998.

* cited by examiner

*Primary Examiner*—Yvonne Eyler
*Assistant Examiner*—Nirmal S. Basi
(74) *Attorney, Agent, or Firm*—Klarquist Sparkman, LLP

(57) ABSTRACT

The invention stems from the discovery that sFRP and fragments thereof can bind to members of the Wnt family of proteins and cause an increase in Wnt biological activity. Furthermore, fragments of sFRP that do not contain the CRD domain are shown to bind to Wnt proteins and modulate Wnt biological activity. Accordingly, the invention provides these sFRP fragments and variants of these fragments, as well as vectors and host cells containing nucleic acid sequences encoding the sFRP fragments and variants.

9 Claims, 6 Drawing Sheets

SEQUENCE LISTING

<160> NUMBER OF SEQ ID NOS: 13

<210> SEQ ID NO 1
<211> LENGTH: 2075
<212> TYPE: DNA
<213> ORGANISM: Homo sapiens

<400> SEQUENCE: 1

```
cctgcagcct ccggagtcag tgccgcgcgc ccgccgcccc gcgccttcct gctcgccgca        60
cctccgggag ccggggcgca cccagcccgc agcgccgcct ccccgcccgc gccgcctccg       120
accgcaggcc gagggccgcc actggccggg gggaccgggc agcagcttgc ggccgcggag       180
ccgggcaacg ctggggactg cgccttttgt ccccggaggt ccctggaagt ttgcggcagg       240
acgcgcgcgg ggaggcggcg gaggcagccc cgacgtcgcg gagaacaggg cgcagagccg       300
gcatgggcat cgggcgcagc gagggggggcc gccgcgggc cctgggcgtg ctgctggcgc       360
tgggcgcggc gcttctggcc gtgggctcgg ccagcgagta cgactacgtg agcttccagt       420
cggacatcgg cccgtaccag agcgggcgct tctacaccaa gccacctcag tgcgtggaca       480
tccccgcgga cctgcggctg tgccacaacg tgggctacaa gaagatggtg ctgcccaacc       540
tgctggagca cgagaccatg gcggaggtga agcagcaggc cagcagctgg gtgcccctgc       600
tcaacaagaa ctgccacgcc gggacccagg tcttcctctg ctcgctcttc gcgcccgtct       660
gcctggaccg gcccatctac ccgtgtcgct ggctctgcga ggccgtgcgc gactcgtgcg       720
agccggtcat gcagttcttc ggcttctact ggcccgagat gcttaagtgt gacaagttcc       780 cggagggggga cgtctgcatc gccatgacgc cgcccaatgc caccgaagcc tccaagcccc       840
aaggcacaac ggtgtgtcct ccctgtgaca acgagttgaa atctgaggcc atcattgaac       900
atctctgtgc cagcgagttt gcactgagga tgaaaataaa agaagtgaaa aagaaaatg       960 gcgacaagaa gattgtcccc aagaagaaga agccctgaa gttggggccc atcaagaaga      1020
aggacctgaa gaagcttgtg ctgtacctga agaatgggc tgactgtccc tgccaccagc      1080
tggacaacct cagccaccac ttcctcatca tgggccgcaa ggtgaagagc cagtacttgc      1140
tgacggccat ccacaagtgg gacaagaaaa acaaggagtt caaaaacttc atgaagaaaa      1200
tgaaaaacca tgagtgcccc acctttcagt ccgtgtttaa gtgattctcc cggggggcagg      1260
```

-continued

```
gtggggaggg agcctcgggt ggggtgggag cgggggggac agtgcccggg aacccgtggt    1320
cacacacacg cactgccctg tcagtagtgg acattgtaat ccagtcggct tgttcttgca    1380
gcattcccgc tcccttccc tccatagcca cgctccaaac cccagggtag ccatggccgg    1440
gtaaagcaag ggccatttag attaggaagg ttttaagat ccgcaatgtg gagcagcagc    1500
cactgcacag gaggaggtga caaaccattt ccaacagcaa cacagccact aaaacacaaa    1560 aaggggatt gggcggaaag tgagagccag cagcaaaaac tacattttgc aacttgttgg    1620
tgtggatcta ttggctgatc tatgccttc aactagaaaa ttctaatgat tggcaagtca    1680
cgttgttttc aggtccagag tagtttcttt ctgtctgctt taaatggaaa cagactcata    1740
ccacacttac aattaaggtc aagcccagaa agtgataagt gcagggagga aaagtgcaag    1800
tccattatct aatagtgaca gcaaagggac caggggagag gcattgcctt ctctgcccac    1860
agtctttccg tgtgattgtc tttgaatctg aatcagccag tctcagatgc ccaaagttt    1920 cggttcctat gagcccgggg catgatctga tccccaagac atgtggaggg gcagcctgtg    1980
cctgcctttg tgtcagaaaa aggaaaccac agtgagcctg agagagacgg cgattttcgg    2040
gctgagaagg cagtagtttt caaaacacat agtta                              2075
```

<210> SEQ ID NO 2
<211> LENGTH: 942
<212> TYPE: DNA
<213> ORGANISM: Homo sapiens

<400> SEQUENCE: 2

```
atgggcatcg gcgcacgga ggggggccgc cgcggggcag ccctgggcgt gctgctggcg    60
ctgggcggcg cttctggccg tgggctcggc agcgagtacg actacgtgag cttccagtcg    120
gacatcggcc cgtaccagag cgggcgcttc tacaccaagc cacctcagtg cgtggacatc    180
cccgcggacc tgcggctgtg ccacaacgtg ggctacaaga gatggtgct gcccaacctg    240 ctggagcacg agaccatggc ggaggtgaag cagcaggcca gcagctgggt gccctgctc    300 aacaagaact gccacgccgg gacccaggtc ttcctctgct cgctcttcgc gcccgtctgc    360
ctggaccggc ccatctaccc gtgtcgctgg ctctgcgagg ccgtgcgcga ctcgtgcgag    420
ccggtcatgc agttcttcgg cttctactgg cccgagatgc ttaagtgtga caagttcccg    480
gagggggacg tctgcatcgc catgacgccg cccaatgcca ccgaagcctc caagcccaa    540 ggcacaacgg tgtgtcctcc ctgtgacaac gagttgaaat ctgaggccat cattgaacat    600
ctctgtgcca gcgagtttgc actgaggatg aaaataaaag aagtgaaaaa gaaaaatggc    660
gacaagaaga ttgtccccaa gaagaagaag cccctgaagt tggggcccat caagaagaag    720
gacctgaaga agcttgtgct gtacctgaag aatggggctg actgtccctg ccaccagctg    780
gacaacctca gccaccactt cctcatcatg ggccgcaagg tgaagagcca gtacttgctg    840
acggccatcc acaagtggga caagaaaaac aaggagttca aaacttcat gaagaaaatg    900 aaaaaccatg agtgccccac ctttcagtcc gtgtttaagt ga                      942
```

<210> SEQ ID NO 3
<211> LENGTH: 313
<212> TYPE: PRT
<213> ORGANISM: Homo sapiens

<400> SEQUENCE: 3

```
Met Gly Ile Gly Arg Thr Glu Gly Gly Arg Arg Gly Ala Ala Leu Gly
  1               5                  10                  15
```

```
Val Leu Leu Ala Leu Gly Gly Ala Ser Gly Arg Gly Leu Gly Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Cys Val Asp Ile Pro Ala Asp Leu
    50                  55                  60

Arg Leu Cys His Asn Val Gly Tyr Lys Lys Met Val Leu Pro Asn Leu
65                  70                  75                  80

Leu Glu His Glu Thr Met Ala Glu Val Lys Gln Gln Ala Ser Ser Trp
                85                  90                  95

Val Pro Leu Leu Asn Lys Asn Cys His Ala Gly Thr Gln Val Phe Leu
            100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
        195                 200                 205

Arg Met Lys Ile Lys Glu Val Lys Lys Glu Asn Gly Asp Lys Lys Ile
    210                 215                 220

Val Pro Lys Lys Lys Lys Pro Leu Lys Leu Gly Pro Ile Lys Lys Lys
225                 230                 235                 240

Asp Leu Lys Lys Leu Val Leu Tyr Leu Lys Asn Gly Ala Asp Cys Pro
                245                 250                 255

Cys His Gln Leu Asp Asn Leu Ser His His Phe Leu Ile Met Gly Arg
            260                 265                 270

Lys Val Lys Ser Gln Tyr Leu Leu Thr Ala Ile His Lys Trp Asp Lys
        275                 280                 285

Lys Asn Lys Glu Phe Lys Asn Phe Met Lys Lys Met Lys Asn His Glu
    290                 295                 300

Cys Pro Thr Phe Gln Ser Val Phe Lys
305                 310

<210> SEQ ID NO 4
<211> LENGTH: 338
<212> TYPE: PRT
<213> ORGANISM: Homo sapiens

<400> SEQUENCE: 4

Met Gly Ile Gly Arg Thr Glu Gly Gly Arg Arg Gly Ala Ala Leu Gly
1               5                   10                  15

Val Leu Leu Ala Leu Gly Gly Ala Ser Gly Arg Gly Leu Gly Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Cys Val Asp Ile Pro Ala Asp Leu
    50                  55                  60

Arg Leu Cys His Asn Val Gly Tyr Lys Lys Met Val Leu Pro Asn Leu
65                  70                  75                  80
```

-continued

```
Leu Glu His Glu Thr Met Ala Glu Val Lys Gln Gln Ala Ser Ser Trp
             85                  90                  95
Val Pro Leu Leu Asn Lys Asn Cys His Ala Gly Thr Gln Val Phe Leu
         100                 105                 110
Cys Ser Leu Phe Ala Pro Val Cys Leu Asp Arg Pro Ile Tyr Pro Cys
         115                 120                 125
Arg Trp Leu Cys Glu Ala Val Arg Asp Ser Cys Glu Pro Val Met Gln
         130                 135                 140
Phe Phe Gly Phe Tyr Trp Pro Glu Met Leu Lys Cys Asp Lys Phe Pro
145                 150                 155                 160
Glu Gly Asp Val Cys Ile Ala Met Thr Pro Pro Asn Ala Thr Glu Ala
                 165                 170                 175
Ser Lys Pro Gln Gly Thr Thr Val Cys Pro Pro Cys Asp Asn Glu Leu
             180                 185                 190
Lys Ser Glu Ala Ile Ile Glu His Leu Cys Ala Ser Glu Phe Ala Leu
         195                 200                 205
Arg Met Lys Ile Lys Glu Val Lys Lys Glu Asn Gly Asp Lys Lys Ile
         210                 215                 220
Val Pro Lys Lys Lys Pro Leu Lys Leu Gly Pro Ile Lys Lys Lys
225                 230                 235                 240
Asp Leu Lys Lys Leu Val Leu Tyr Leu Lys Asn Gly Ala Asp Cys Pro
                 245                 250                 255
Cys His Gln Leu Asp Asn Leu Ser His His Phe Leu Ile Met Gly Arg
             260                 265                 270
Lys Val Lys Ser Gln Tyr Leu Leu Thr Ala Ile His Lys Trp Asp Lys
         275                 280                 285
Lys Asn Lys Glu Phe Lys Asn Phe Met Lys Met Lys Asn His Glu
         290                 295                 300
Cys Pro Thr Phe Gln Ser Val Phe Lys Gln Ala Tyr Val Glu Gln Lys
305                 310                 315                 320
Leu Ile Ser Glu Glu Asp Leu Asn Ser Ala Val Asp His His His His
                 325                 330                 335
His His
```

```
<210> SEQ ID NO 5
<211> LENGTH: 195
<212> TYPE: PRT
<213> ORGANISM: Homo sapiens

<400> SEQUENCE: 5

Met Gly Ile Gly Arg Thr Glu Gly Gly Arg Gly Ala Ala Leu Gly
  1               5                  10                  15
Val Leu Leu Ala Leu Gly Gly Ala Ser Gly Arg Gly Leu Gly Ser Glu
             20                  25                  30
Tyr Asp Tyr Val Ser Phe Gln Ser Asp Ile Gly Pro Tyr Gln Ser Gly
         35                  40                  45
Arg Phe Tyr Thr Lys Pro Pro Gln Cys Val Asp Ile Pro Ala Asp Leu
     50                  55                  60
Arg Leu Cys His Asn Val Gly Tyr Lys Lys Met Val Leu Pro Asn Leu
 65                  70                  75                  80
Leu Glu His Glu Thr Met Ala Glu Val Lys Gln Gln Ala Ser Ser Trp
             85                  90                  95
Val Pro Leu Leu Asn Lys Asn Cys His Ala Gly Thr Gln Val Phe Leu
         100                 105                 110
```

-continued

```
Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Gln Ala Tyr Val Glu Gln
                165                 170                 175

Lys Leu Ile Ser Glu Glu Asp Leu Asn Ser Ala Val Asp His His
            180                 185                 190

His His His
        195

<210> SEQ ID NO 6
<211> LENGTH: 246
<212> TYPE: PRT
<213> ORGANISM: Homo sapiens

<400> SEQUENCE: 6

Met Gly Ile Gly Arg Thr Glu Gly Gly Arg Gly Ala Ala Leu Gly
1               5                   10                  15

Val Leu Ala Leu Gly Gly Ala Ser Gly Arg Gly Leu Gly Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Cys Val Asp Ile Pro Ala Asp Leu
    50                  55                  60

Arg Leu Cys His Asn Val Gly Tyr Lys Lys Met Val Leu Pro Asn Leu
65                  70                  75                  80

Leu Glu His Glu Thr Met Ala Glu Val Lys Gln Gln Ala Ser Ser Trp
                85                  90                  95

Val Pro Leu Leu Asn Lys Asn Cys His Ala Gly Thr Gln Val Phe Leu
            100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
        195                 200                 205

Arg Met Lys Ile Lys Glu Val Lys Lys Glu Asn Gly Asp Gln Ala Tyr
    210                 215                 220

Val Glu Gln Lys Leu Ile Ser Glu Glu Asp Leu Asn Ser Ala Val Asp
225                 230                 235                 240

His His His His His His
                245

<210> SEQ ID NO 7
<211> LENGTH: 267
<212> TYPE: PRT
```

<213> ORGANISM: Homo sapiens

<400> SEQUENCE: 7

```
Met Gly Ile Gly Arg Thr Glu Gly Gly Arg Arg Gly Ala Ala Leu Gly
 1               5                  10                  15

Val Leu Leu Ala Leu Gly Gly Ala Ser Gly Arg Gly Leu Gly Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Cys Val Asp Ile Pro Ala Asp Leu
 50                  55                  60

Arg Leu Cys His Asn Val Gly Tyr Lys Lys Met Val Leu Pro Asn Leu
 65                  70                  75                  80

Leu Glu His Glu Thr Met Ala Glu Val Lys Gln Gln Ala Ser Ser Trp
                85                  90                  95

Val Pro Leu Leu Asn Lys Asn Cys His Ala Gly Thr Gln Val Phe Leu
            100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
        195                 200                 205

Arg Met Lys Ile Lys Glu Val Lys Lys Glu Asn Gly Asp Lys Lys Ile
210                 215                 220

Val Pro Lys Lys Lys Pro Leu Lys Leu Gly Pro Ile Lys Lys Lys
225                 230                 235                 240

Asp Leu Gln Ala Tyr Val Glu Gln Lys Leu Ile Ser Glu Glu Asp Leu
                245                 250                 255

Asn Ser Ala Val Asp His His His His His
            260                 265
```

<210> SEQ ID NO 8
<211> LENGTH: 229
<212> TYPE: PRT
<213> ORGANISM: Homo sapiens

<400> SEQUENCE: 8

```
Met Gly Ile Gly Arg Thr Glu Gly Gly Arg Arg Gly Ala Ala Leu Gly
 1               5                  10                  15

Val Leu Leu Ala Leu Gly Gly Ala Ser Gly Arg Gly Leu Gly Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Ile Ala Met Thr Pro Pro Asn Ala
 50                  55                  60

Thr Glu Ala Ser Lys Pro Gln Gly Thr Thr Val Cys Pro Pro Cys Asp
 65                  70                  75                  80

Asn Glu Leu Lys Ser Glu Ala Ile Ile Glu His Leu Cys Ala Ser Glu
```

|  |  |  | 85 |  |  |  | 90 |  |  |  | 95 |  |
|---|---|---|---|---|---|---|---|---|---|---|---|---|

Phe Ala Leu Arg Met Lys Ile Lys Glu Val Lys Lys Glu Asn Gly Asp
                     100                   105               110

Lys Lys Ile Val Pro Lys Lys Lys Pro Leu Lys Leu Gly Pro Ile
        115               120               125

Lys Lys Lys Asp Leu Lys Lys Leu Val Leu Tyr Leu Lys Asn Gly Ala
 130                 135                   140

Asp Cys Pro Cys His Gln Leu Asp Asn Leu Ser His Phe Leu Ile
145               150               155              160

Met Gly Arg Lys Val Lys Ser Gln Tyr Leu Leu Thr Ala Ile His Lys
            165               170              175

Trp Asp Lys Lys Asn Lys Glu Phe Lys Asn Phe Met Lys Lys Met Lys
        180               185               190

Asn His Glu Cys Pro Thr Phe Gln Ser Val Phe Lys Gln Ala Tyr Val
        195               200              205

Glu Gln Lys Leu Ile Ser Glu Glu Asp Leu Asn Ser Ala Val Asp His
 210                 215                   220

His His His His His
225

<210> SEQ ID NO 9
<211> LENGTH: 1017
<212> TYPE: DNA
<213> ORGANISM: Homo sapiens

<400> SEQUENCE: 9

| atgggcatcg | ggcgcacgga | gggggggccgc | cgcggggcag | ccctgggcgt | gctgctggcg | 60 |
|---|---|---|---|---|---|---|
| ctgggcggcg | cttctggccg | tgggctcggc | agcgagtacg | actacgtgag | cttccagtcg | 120 |
| gacatcggcc | cgtaccagag | cgggcgcttc | tacaccaagc | cacctcagtg | cgtggacatc | 180 |
| cccgcggacc | tgcggctgtg | ccacaacgtg | ggctacaaga | gatggtgct | gcccaacctg | 240 |
| ctggagcacg | agaccatggc | ggaggtgaag | cagcaggcca | gcagctgggt | gcccctgctc | 300 |
| aacaagaact | gccacgccgg | gacccaggtc | ttcctctgct | cgctcttcgc | gcccgtctgc | 360 |
| ctggaccggc | ccatctaccc | gtgtcgctgg | ctctgcgagg | ccgtgcgcga | ctcgtgcgag | 420 |
| ccggtcatgc | agttcttcgg | cttctactgg | cccgagatgc | ttaagtgtga | caagttcccg | 480 |
| gagggggacg | tctgcatcgc | catgacgccg | cccaatgcca | ccgaagcctc | caagccccaa | 540 |
| ggcacaacgg | tgtgtcctcc | ctgtgacaac | gagttgaaat | ctgaggccat | cattgaacat | 600 |
| ctctgtgcca | gcgagtttgc | actgaggatg | aaaataaaag | aagtgaaaaa | agaaaatggc | 660 |
| gacaagaaga | ttgtccccaa | gaagaagaag | cccctgaagt | tggggcccat | caagaagaag | 720 |
| gacctgaaga | agcttgtgct | gtacctgaag | aatggggctg | actgtccctg | ccaccagctg | 780 |
| gacaacctca | gccaccactt | cctcatcatg | ggccgcaagg | tgaagagcca | gtacttgctg | 840 |
| acggccatcc | acaagtggga | caagaaaaac | aaggagttca | aaacttcat | gaagaaaatg | 900 |
| aaaaccatg | agtgccccac | ctttcagtcc | gtgtttaagc | aagcttacgt | agaacaaaaa | 960 |
| ctcatctcag | aagaggatct | gaatagcgcc | gtcgaccatc | atcatcatca | tcattga | 1017 |

<210> SEQ ID NO 10
<211> LENGTH: 588
<212> TYPE: DNA
<213> ORGANISM: Homo sapiens

<400> SEQUENCE: 10

| | |
|---|---|
| atgggcatcg ggcgcacgga ggggggccgc cgcggggcag ccctgggcgt gctgctggcg | 60 |
| ctgggcggcg cttctggccg tgggctcggc agcgagtacg actacgtgag cttccagtcg | 120 |
| gacatcggcc cgtaccagag cgggcgcttc tacaccaagc cacctcagtg cgtggacatc | 180 |
| cccgcggacc tgcggctgtg ccacaacgtg ggctacaaga agatggtgct gcccaacctg | 240 |
| ctggagcacg agaccatggc ggaggtgaag cagcaggcca gcagctgggt gcccctgctc | 300 |
| aacaagaact gccacgccgg gacccaggtc ttcctctgct cgctcttcgc gcccgtctgc | 360 |
| ctggaccggc ccatctaccc gtgtcgctgg ctctgcgagg ccgtgcgcga ctcgtgcgag | 420 |
| ccggtcatgc agttcttcgg cttctactgg cccgagatgc ttaagtgtga caagttcccg | 480 |
| gagggggacg tctgcatcgc catgacgccg caagcttacg tagaacaaaa actcatctca | 540 |
| gaagaggatc tgaatagcgc cgtcgaccat catcatcatc atcattga | 588 |

<210> SEQ ID NO 11
<211> LENGTH: 741
<212> TYPE: DNA
<213> ORGANISM: Homo sapiens

<400> SEQUENCE: 11

| | |
|---|---|
| atgggcatcg ggcgcacgga ggggggccgc cgcggggcag ccctgggcgt gctgctggcg | 60 |
| ctgggcggcg cttctggccg tgggctcggc agcgagtacg actacgtgag cttccagtcg | 120 |
| gacatcggcc cgtaccagag cgggcgcttc tacaccaagc cacctcagtg cgtggacatc | 180 |
| cccgcggacc tgcggctgtg ccacaacgtg ggctacaaga agatggtgct gcccaacctg | 240 |
| ctggagcacg agaccatggc ggaggtgaag cagcaggcca gcagctgggt gcccctgctc | 300 |
| aacaagaact gccacgccgg gacccaggtc ttcctctgct cgctcttcgc gcccgtctgc | 360 |
| ctggaccggc ccatctaccc gtgtcgctgg ctctgcgagg ccgtgcgcga ctcgtgcgag | 420 |
| ccggtcatgc agttcttcgg cttctactgg cccgagatgc ttaagtgtga caagttcccg | 480 |
| gagggggacg tctgcatcgc catgacgccg cccaatgcca ccgaagcctc caagccccaa | 540 |
| ggcacaacgg tgtgtcctcc ctgtgacaac gagttgaaat ctgaggccat cattgaacat | 600 |
| ctctgtgcca gcgagtttgc actgaggatg aaaataaaag aagtgaaaaa agaaaatggc | 660 |
| gaccaagctt acgtagaaca aaaactcatc tcagaagagg atctgaatag cgccgtcgac | 720 |
| catcatcatc atcatcattg a | 741 |

<210> SEQ ID NO 12
<211> LENGTH: 804
<212> TYPE: DNA
<213> ORGANISM: Homo sapiens

<400> SEQUENCE: 12

| | |
|---|---|
| atgggcatcg ggcgcacgga ggggggccgc cgcggggcag ccctgggcgt gctgctggcg | 60 |
| ctgggcggcg cttctggccg tgggctcggc agcgagtacg actacgtgag cttccagtcg | 120 |
| gacatcggcc cgtaccagag cgggcgcttc tacaccaagc cacctcagtg cgtggacatc | 180 |
| cccgcggacc tgcggctgtg ccacaacgtg ggctacaaga agatggtgct gcccaacctg | 240 |
| ctggagcacg agaccatggc ggaggtgaag cagcaggcca gcagctgggt gcccctgctc | 300 |
| aacaagaact gccacgccgg gacccaggtc ttcctctgct cgctcttcgc gcccgtctgc | 360 |
| ctggaccggc ccatctaccc gtgtcgctgg ctctgcgagg ccgtgcgcga ctcgtgcgag | 420 |
| ccggtcatgc agttcttcgg cttctactgg cccgagatgc ttaagtgtga caagttcccg | 480 |
| gagggggacg tctgcatcgc catgacgccg cccaatgcca ccgaagcctc caagccccaa | 540 |

-continued

```
ggcacaacgg tgtgtcctcc ctgtgacaac gagttgaaat ctgaggccat cattgaacat      600
ctctgtgcca gcgagtttgc actgaggatg aaaataaaag aagtgaaaaa agaaaatggc      660
gacaagaaga ttgtccccaa gaagaagaag ccctgaagt tggggcccat caagaagaag       720
gacctgcaag cttacgtaga acaaaaactc atctcagaag aggatctgaa tagcgccgtc      780
gaccatcatc atcatcatca ttga                                              804

<210> SEQ ID NO 13
<211> LENGTH: 690
<212> TYPE: DNA
<213> ORGANISM: Homo sapiens

<400> SEQUENCE: 13
atgggcatcg ggcgcacgga gggggccgc cgcggggcag ccctgggcgt gctgctggcg        60
ctgggcggcg cttctggccg tgggctcggc agcgagtacg actacgtgag cttccagtcg      120
gacatcggcc cgtaccagag cgggcgcttc tacaccaagc cacctcagat cgccatgacg      180
ccgcccaatg ccaccgaagc ctccaagccc caaggcacaa cggtgtgtcc tccctgtgac      240
aacgagttga aatctgaggc catcattgaa catctctgtg ccagcgagtt tgcactgagg      300
atgaaaataa aagaagtgaa aaagaaaat ggcgacaaga agattgtccc caagaagaag       360
aagcccctga agttggggcc catcaagaag aaggacctga agaagcttgt gctgtacctg      420
aagaatgggg ctgactgtcc ctgccaccag ctggacaacc tcagccacca cttcctcatc      480
atgggccgca aggtgaagag ccagtacttg ctgacggcca tccacaagtg ggacaagaaa      540
aacaaggagt tcaaaaactt catgaagaaa atgaaaaacc atgagtgccc caccttcag      600 tccgtgttta agcaagctta cgtagaacaa aaactcatct cagaagagga tctgaatagc      660
gccgtcgacc atcatcatca tcatcattga                                        690
```

US 6,600,018 B1

SECRETED FRIZZLED RELATED PROTEIN, SFRP, FRAGMENTS AND METHODS OF USE THEREOF

FIELD OF THE INVENTION

This invention relates to use of sFRP fragments and variants thereof to bind to members of the Wnt family of proteins and regulate Wnt biological activity.

BACKGROUND

Wnt proteins comprise a large family of structurally related, extracellular agents that have a variety of important functions during embryonic development (Cadigan and Nusse, *Genes Dev.* 11:3286–3305, 1997 and Dale, T. C., *Biochem J.* 329:209–223, 1998). They specify cell polarity and fate, stimulate proliferation, and contribute to the patterning of tissue in many animal models. Wnt signaling also has been strongly implicated in the development of neoplasia.

A set of secreted Fz-related proteins (sFRP or FRP) recently have been described (Leyns et al., *Cell* 88:747–756, 1997; Wang et al., *Cell* 88:757–766, 1997; Rattner et al., *Proc. Natl. Acad. Sci. U.S.A.* 94:2859–2863, 1997; Finch et al., *Proc. Natl. Acad. Sci. U.S.A.* 94:6770–6775, 1997; Salic et al., *Development* 124:4739–4748, 1997; Melkonyan et al., *Proc. Natl. Acad. Sci. U.S.A.* 94:13636–13641, 1997; Pfeffer et al., *Int. J. Dev. Biol.* 41:449–458, 1997; Mayr et al., *Mech. Dev.* 63:109–125, 1997; Wolf et al., *FEBS Lett.* 417:385–389, 1997; Xu et al., *Development* 125:4767–4776, 1998; Chang et al., *Hum. Mol. Genet.* 8:575–583 1999; and Abu-Jawdeh et al., *Lab. Invest.* 79:439–447, 1999). These proteins consist of approximately 300 amino acids, including a CRD (cysteine rich domain) that is typically 30–50% identical to the CRDs of Fz family members. The carboxyl-terminal portion of these proteins often contains segments rich in positively charged residues, and two (sFRP-1 and FrzB/sFRP-3) were reported to bind tightly to heparin (Finch et al., *Proc. Natl. Acad. Sci. U.S.A.* 94:6770–6775, 1997 and Hoang et al., *J. Biol Chem.* 271:26131–26137, 1996). The CRD has been also found to be the Wnt binding site based on several experiments in which the Fz CRD conferred Wnt binding and/or responsiveness (Hsieh et al., *Proc. Natl. Acad. Sci. U.S.A.* 96:3546–3551, 1999; Bhanot et al., *Nature* 382:225–230, 1996; and He et al., *Science* 275:1652–1654, 1997).

SUMMARY

The invention stems from the discovery that sFRP and fragments thereof can bind to members of the Wnt family of proteins, and furthermore that these molecules have a biphasic effect on Wnt activity. At high concentrations these proteins inhibit Wnt activity and at low concentrations these proteins increase in Wnt biological activity. Furthermore, fragments of sFRP that do not contain the CRD domain are provided and these fragments are shown to bind to Wnt proteins and modulate Wnt biological activity.

Accordingly, the invention provides fragments of sFRP which are able to bind to Wnt thereby modulating Wnt biological activity. These sFRP fragments may (SEQ ID NOS: 5–7) or may not (SEQ ID NO: 8) contain the CRD of sFRP. Because these fragments bind to Wnt these fragments, and variants thereof, can be used to screen for other molecules that bind to Wnt and modulate Wnt activity.

The invention also provides methods of using sFRP-1 and fragments thereof to increase Wnt biological activity. The increase in Wnt activity is desirable for treating developmental disorders that are associated with decreased Wnt biological activity as well as for inducing the development of neoplasias which is desirable in experimental models for the study of tumor growth.

The invention also provides methods of using sFRP without the CRD domain to increase or decrease Wnt biological activity depending upon the amount provided. Such methods are useful for treating disorders associated with increased Wnt biological activity and for the suppression of tumor growth. Furthermore, the finding that sFRP fragments without the CRD domain bind to Wnt proteins allows for the development of screening assays which identify small molecules or other compounds which may block sFRP/Wnt binding or enhance sFRP/Wnt binding. Thus, for example, the invention provides methods of identifying small molecules or binding proteins that bind either Wnt or fragments of sFRP without the CRD and disrupt sFRP/Wnt binding.

Accordingly, another aspect of the invention provides methods of modulating Wnt protein biological activity. These methods involve contacting at least one Wnt protein with least one sFRP fragment or variant thereof and producing an increase Wnt biological activity.

Yet another aspect of the invention provides a sFRP fragment that does not contain the CRD portion of sFRP (SEQ ID NO: 8), but yet maintains Wnt binding activity. Accordingly this fragment and variants thereof can be used to screen for other molecules that bind to Wnt and modulate Wnt biological activity.

When used to modulate Wnt biological activity the fragments described above can be used to further characterize the biological role that Wnt plays in the various developmental processes. Furthermore, these fragments can also be used to modulate conditions associated with abnormal Wnt biological activity.

BRIEF DESCRIPTION OF THE DRAWINGS

FIG. 1A is a graph that shows the isolation of sFRP-1 from sFRP-1/MDCK cells (ATCC NO. CCL-34) as the sFRP-1 was eluted from a heparin-Sepharose resin (bed volume, 1 ml). Samples were eluted with increasing NaCl concentration (dashed line), and protein content was assessed by measuring optical density at 280 nm (solid line). Fractions (1 ml) are indicated on the horizontal axis. The thick bar indicates fractions containing sFRP-1. FIG. 1B is a 12% SDS-PAGE gel in which selected fractions from the heparin-Sepharose resin (described in A) were separated in. The protein bands were visualized by silver staining. The molar concentration of NaCl for eluted fractions is indicated above the lanes. The positions of molecular mass markers are shown at the left. The inset shows silver staining of three 1.0 M NaCl fractions resolved in an 8% polyacrylamide gel. FIG. 1C is an anti-sFRP-1 immunoblot. The samples are from the same fractions viewed in B, again separated by 12% SDS-PAGE. FIG. 1D is an anti-sFRP-1 immunoblot of conditioned media from clonal lines derived from sFRP-1/MDCK mass culture.

FIG. 2A is a schematic of sFRP-1 and its derivatives. Numbers indicate amino acid residues in sFRP-1 sequence at boundaries of recombinant proteins. CRD (hatched boxes) borders also are shown. The white boxes correspond to lysine-rich segments. M/H indicates the Myc-His epitope tags. FIG. 2B is an anti-Myc immunoblot (left panel) and silver stain (right panel) analysis of purified sFRP-1 mutant proteins. The positions of molecular mass markers are indicated at the left. FIG. 2C is an immunoblot showing the elution pattern of the sFRP-1 derivatives from a heparin-sepharose. The derivatives were isolated from conditioned media from MDCK cells transfected with sFRP-1 derivatives and applied to heparin-Sepharose columns. Samples were eluted with indicated concentrations of NaCl, and fractions were analyzed by Western blotting with anti-Myc.

FIG. 3A is a graph of the results from an ELISA. Wells were coated with sFRP-1 or BSA alone and incubated with dilutions of Wg-containing or S2 control medium. Bound Wg protein was detected with anti-Wg and secondary immune reagents as described under "Experimental Procedures. " FIG. 3B is a gel showing the Wg cross-reactive protein pattern from conditioned media from control S2 or Wg-expressing S2 cells that were analyzed by immunoblotting with anti-Wg. The arrow at the right indicates primary Wg band. Positions of molecular mass markers are shown at the left. FIG. 1C is a graph showing the results from an ELISA. Wells were coated with sFRP-1 derivatives and incubated with indicated dilutions of conditioned media containing Wg. FIG. 3D is a graph showing the results from another ELISA. Wells were coated with sFRP-1 and incubated with Wg-containing media that had been pre-incubated with the indicated concentrations of sFRP-1 derivatives. Each panel is representative of several experiments.

FIG. 5B is gel showing the results from a competition assay with unlabeled sFRP-1. FIG. 5C is another gel showing the effect of varying heparin concentrations on cross-linking.

FIG. 6A is a gel showing the results from DFz2-expressing S2 cells that were incubated with Wg medium at the indicated concentrations of sFRP-1. Cell lysates were analyzed by immunoblotting with anti-Arm (upper panel) and anti-HSP70 (lower panel). Similar experiments as in A were preformed with sFRP-M/H (SEQ ID NO: 4; B), sFRP-ΔCRD (SEQ ID NO: 8; C), and sFRP-Δ2 (SEQ ID NO: 6; D). Each panel is representative of three to five separate experiments.

SEQUENCE LISTING

Figure 1:
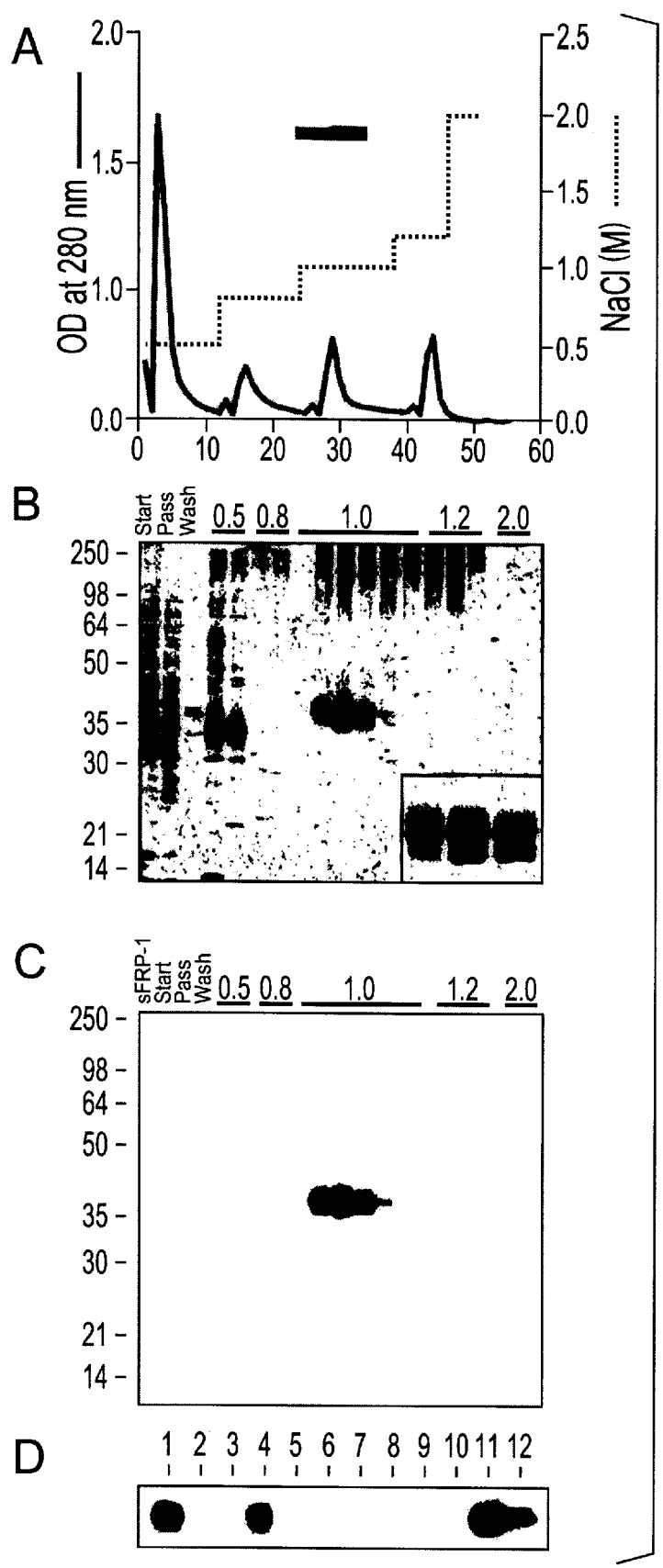
FIGS. 1A–1D include a graph and three gels that depict the results from the purification of recombinant sFRP-1.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the cDNA sequence of human sFRP-1.

SEQ ID NO: 2 shows the nucleic acid sequence of the human sFRP-1 open reading frame.

SEQ ID NO: 3 shows the amino acid sequence of human sFRP-1.

SEQ ID NO: 4 shows the amino acid sequence of human sFRP-1-M/H.

SEQ ID NO: 5 shows the amino acid sequence of human sFRP-Δ1.

SEQ ID NO: 6 shows the amino acid sequence of human sFRP-Δ2.

SEQ ID NO: 7 shows the amino acid sequence of human sFRP-Δ3.

SEQ ID NO: 8 shows the amino acid sequence of human sFRP-ΔCRD.

SEQ ID NO: 9 shows the nucleic acid sequence encoding sFRP-1-M/H.

SEQ ID NO: 10 shows the nucleic acid sequence encoding sFRP-Δ1.

SEQ ID NO: 11 shows the nucleic acid sequence encoding sFRP-Δ2.

SEQ ID NO: 12 shows the nucleic acid sequence encoding sFRP-Δ3.

SEQ ID NO: 13 shows the nucleic acid sequence encoding sFRP-ΔCRD.

DETAILED DESCRIPTION

I. Abbreviations

Arm, armadillo protein; CRD, cysteine-rich domain; sFRP, secreted Frizzled-related protein; MDCK, Madin-Darby canine kidney; BSA, bovine serum albumin; HSPG, heparin-sulfate proteoglycan; ELISA, enzyme-linked immunosorbent assay; PAGE, polyacrylamide gel electrophoresis; PBS, phosphate-buffered saline; mAb, monoclonal antibody; BS 3 , Wnt, Wnt proteins; bis(sulfosuccinimidyl) suberate; M/H, Myc-His epitope tags.

II. Definitions

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

sFRP: sFRP is a secreted protein that consists of approximately 300 amino acids, including a CRD that is typically between 30% and 50% identical to the CRDs of the Fz protein family members. There are several different sFRP proteins and the nucleic acid sequence of the prototypical member, sFRP-1, is provided in SEQ ID NO: 1. The nucleic acid and amino acid sequences of other members of the sFRP family can be found at the National Center for Biotechnology Website, for example under the accession numbers, AF218056 (Gallus gallus FRP-2), AV354083 (Mus musculus-FRP-1), AV304328 (Mus musculus s-FRP-2), U24163 (*homo sapiens* sFRP-3/FrzB) and AI587049 (*Homo sapiens* sFRP-1). The open reading frame of the prototypical sFRP is shown in SEQ. ID NO: 2, while the sequence of the protein is shown in SEQ. ID NO: 3. The present invention takes advantage of the discovery that particular sFRP and fragments of sFRP can increase Wnt biological activity. Furthermore, this activity and binding to Wnt proteins generally is shown not to be dependent upon the CRD region of sFRP.

sFRP-1 binding activity and its ability to modulate Wnt biological activity may be assayed by methods described herein. The ability of a fragment of sFRP-1 protein to perform these activities is believed to be beneficial in a number of applications, including clinical applications such as tumor therapy and treatment of diseases with abnormal Wnt activity.

While the amino acid sequence of the prototypical sFRP is shown in SEQ. ID NO: 3, one of skill in the art will appreciate that variations in this amino acid sequence, such as 1, 2, 5, or 10, deletions, additions, or substitutions, may be made without substantially affecting the activities of the protein (or fragments of the protein) discussed above. Thus, the term "sFRP" fragments encompasses both the proteins having the amino acid sequences shown in SEQ. ID NOs: 4–8, as well as amino acid sequences that are based on these sequences but which include one or more sequence variants. Such sequence variants may also be defined in the degree of amino acid sequence identity that they share with the amino acid sequence shown in SEQ. ID NOs: 4–8. Typically, sFRP sequence variants will share at least 80% sequence identity with the sequences shown in SEQ. ID NOs: 4–8. More highly conserved variants will share at least 90%, at least 95%, or at least 98% sequence identity with the sequences shown in SEQ. ID NOs: 4–8. In addition to sharing sequence identity with the prototypical sFRP protein sequence, such sequence variants possess the ability to bind to Wnt proteins and/or modulate Wnt biological activity.

Oligonucleotide: A linear polynucleotide sequence of up to about 100 nucleotide bases in length.

Polypeptide: A protein fragment including at least two amino acid residues.

Polynucleotide: A nucleic acid sequence including at least two nucleic acid residues.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. A vector may also include a sequence encoding for an amino acid motif that facilitates the isolation of the desired protein product such as a sequence encoding maltose binding protein, c-myc, or GST.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of sFRP will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237–244, 1988; Higgins and Sharp, *CABIOS* 5:151–153, 1989; Corpet et al., *Nucleic Acids Research* 16:10881–10890, 1988; and Pearson and Lipman, *Proc. Natl. Acad. Sci. U.S.A.* 85:2444, 1988. Altschul et al., *Nature Genet.* 6:119–129, 1994.

The NCBI Basic Local Alignment Search Tool (BLAST™) (Altschul et al., *J. Mol. Biol.* 215:403–410, 1990.) is available from several sources, including the National Center for Biotechnology Information (NCBI, Bethesda, Md.) and on the Internet, for use in connection with the sequence analysis programs blastp, blastn, blastx, tblastn and tblastx.

Variants of sFRP fragments are typically characterized by possession of at least 50% sequence identity counted over the full length alignment with the amino acid sequence of the sFRP fragment using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, homologs and variants will typically possess at least 75% sequence identity over short windows of 10–20 amino acids, and may possess sequence identities of at least 85% or at least 90% or 95% depending on their similarity to the reference sequence. Methods for determining sequence identity over such short windows are described at the website that is maintained by the National Center for Biotechnology Information in Bethesda, Md. One of skill in the art will appreciate that these sequence identity ranges are provided for guidance only; it is entirely possible that strongly significant homologs could be obtained that fall outside of the ranges provided.

CRD: A cysteine rich domain that typically is about 120 amino acids in length and found on the amino terminal half of Fz proteins. In the prototypical sFRP described herein the CRD stretches from amino acid number 57 through 165.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

cDNA (complementary DNA): A piece of DNA lacking internal, non-coding segments (introns) and regulatory sequences that determine transcription. cDNA is synthesized in the laboratory by reverse transcription from messenger RNA extracted from cells.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Subject: Living multi-cellular vertebrate organisms, a category that includes both human and non-human mammals.

Mimetic: A molecule (such as an organic chemical compound) that mimics the activity of a protein, such as a sFRP fragment and variants thereof. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides having substantial specific inhibitory activity or agonist activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., *Pharmaceutical Biotechnology*, Interpharm Press: Buffalo Grove, Ill., pp. 165–174, 1993 and *Principles of Pharmacology* (ed. Munson), chapter 102, 1995, for a description of techniques used in computer assisted drug design.

These and other aspects of the invention are explained in more detail in the following sections. Additionally, throughout the specification and claims, reference to the singular (such as "a" or "the") includes the plural, unless clearly indicated otherwise by context.

III. Development of Methods of Controlling the Biological Activity of Wnt

A. Results

1. Recombinant Expression of sFRP-1 and its Derivatives for Functional Studies

To generate a plentiful supply of sFRP-1 protein, MDCK cells were transfected with a pcDNA3.1 vector containing the coding sequence of human sFRP-1 (SEQ ID NO: 2). MDCK cells have favorable properties for recombinant expression because they grow rapidly and, once confluent, can remain attached to plastic for several weeks in serum-free medium. Consequently, several sequential harvests of conditioned medium can be collected from the same monolayer. A one-step preparative scheme involving heparin-Sepharose affinity chromatography was sufficient to purify sFRP-1 from concentrated conditioned medium (FIG. 1A). Typically 0.25–0.50 mg of sFRP-1/liter of medium was recovered from the transfected mass culture. Silver staining and immunoblot analysis confirmed the purity and identity of the recombinant protein that eluted from heparin-Sepharose with 1.0 M NaCl (FIG. 1, B and C). The protein band in both analyses usually was broad and occasionally resolved into two or three components (FIG. 1B, inset), indicative of microheterogeneity.

The individual components resolved in the blotting procedure described above were identified by microsequencing. The microsequencing revealed that the majority of the protein had an amino-terminal sequence beginning at Ser-31, one residue downstream from the proposed signal peptide cleavage site (Finch et al., *Proc. Natl. Acad. Sci. U.S.A.* 94:6770–6775, 1997). Two other sequences, beginning at Asp-41 and Phe-50, also were obtained and presumably resulted from partial proteolysis. Glycosylation may account for additional heterogeneity.

To optimize the yield of recombinant protein, clonal lines were isolated from the mass culture, and their conditioned media were screened for sFRP-1 content (FIG. 1D). Clone 11 cells (lane 11 in FIG. 1D) were expanded for large scale preparations and yielded 2–4 mg of sFRP-1/liter of conditioned medium.

Figure 2:
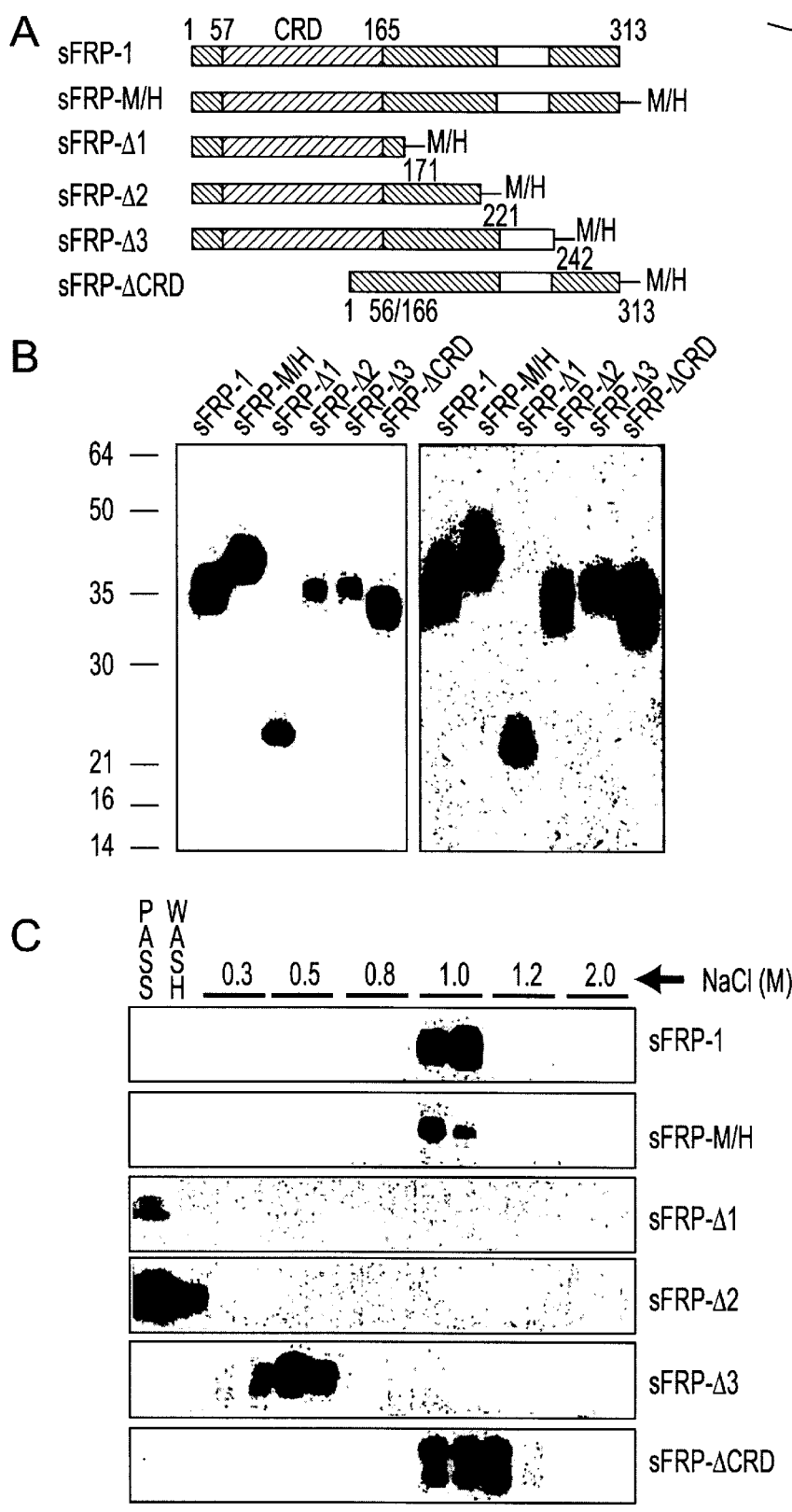
FIGS. 2A–2C included a schematic diagram of the relationship between the various sFRP-1 derivatives, an immunoblot using the various sFRP-1 derivatives, and a gel showing the elution profile of the various sFRP-1 derivatives. These FIGS. taken together identify the sFRP-1 heparin-binding domain.

The deletion mutants that were generated allowed for the correlation of binding properties with particular regions of the sFRP-1 molecule. To facilitate detection and purification of the deletion mutant c-Myc and polyhistidine epitope tags were attached to the carboxyl terminus of each derivative (FIG. 2A). The sFRP-Δ1 (SEQ ID NO: 5) sequence extends through amino acid residue 171, a short distance, beyond the CRD. sFRP-Δ2 (SEQ ID NO: 6) and sFRP-Δ3 (SEQ ID NO: 7) contain progressively more of the carboxyl-terminal region. Included within sFRP-Δ3 (SEQ ID NO: 7) is a lysine-rich domain previously identified as a consensus binding site for hyaluronic acid (Finch et al., *Proc. Natl. Acad. Sci. U.S.A.* 94:6770–6775, 1997). Finally, the sFRP-ΔCRD (SEQ ID NO: 8) deletion mutant was generated such that it lacks the CRD but contains the remaining amino-terminal and entire carboxyl-terminal sequences.

All the sFRP-1 derivatives were readily secreted. and remained in solution after ultrafiltration, chromatography, dialysis, and repeated freeze-thawing, suggesting that there were no gross defects in folding. The proteins were purified to homogeneity by using nickel resin chromatography (FIG. 2B). Initial characterization of these molecules focused on their heparin-binding properties because of the potential importance of this binding trait to the interaction with Wnt proteins. Although full-length sFRP-1 labeled with the c-Myc and histidine tags (sFRP-M/H; SEQ ID NO: 4) eluted from heparin-Sepharose in the same position as native sFRP-1, sFRP-Δ1 (SEQ ID NO: 5) and sFRP-Δ2 (SEQ ID NO: 6) were not retained on the resin (FIG. 2C). Inclusion of the lysine-rich segment in sFRP-Δ3 (SEQ ID NO: 7) resulted in a protein with intermediate heparin-binding capability, eluting with 0.5 M NaCl. This implied that the heparin-binding properties of intact sFRP-1 probably involve multiple sites distributed in the carboxyl-terminal third of the molecule. Consistent with this view, sFRP-ΔCRD (SEQ ID NO: 8) bound heparin-Sepharose in a manner similar to that of the native protein (FIG. 2C).

Figure 3:
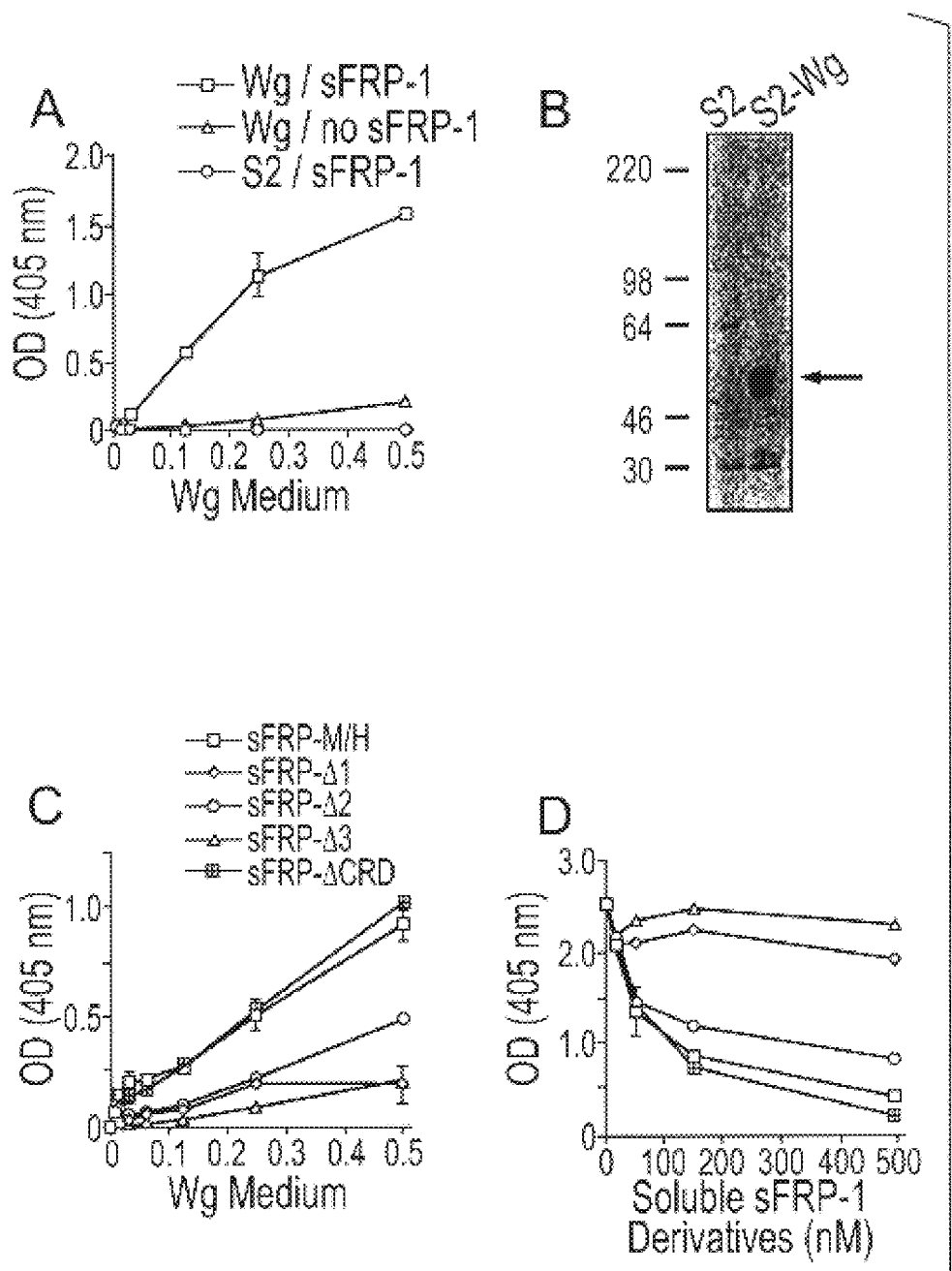
FIGS 3A–3D include a gel and three graphs which show the results of an ELISA demonstrating sFRP-1/Wg binding.

2. Binding Assays with Recombinant sFRP-1 and Derivatives, Using Wingless (Wg) as a WNT Prototype Wingless (Wg) is a gene that was discovered in *Drosophila melanogaster* that codes for a protein in the WNT family. The various assays described below show that Wg binds to sFRP-1. First, an ELISA was used to measure sFRP-1 binding to Wg. Wells were coated with purified full-length sFRP-1 and then blocked with an excess of BSA. Subsequently, conditioned medium from S2HSWg cells expressing soluble Wg was incubated in the wells overnight at room temperature. As a control, aliquots of the same medium were incubated in wells treated with BSA but not sFRP-1. In addition, other wells coated with sFRP-1 were incubated with medium from S2 cells that did not express Wg. As illustrated in FIG. 3A, Wg bound specifically to the wells coated with sFRP-1, and the amount of bound Wg varied with the dilution of Wg medium. In contrast, little Wg was detected in wells that had not been treated with sFRP-1, and no signal was observed when medium lacking Wg was used in the assay (FIG. 3, A and B). These results indicate that sFRP-1 can bind Wg and presumably other Wnt proteins as well.

Based on these findings, a similar analysis was performed using wells coated with the various sFRP-1 deletion mutants (FIG. 3C). Surprisingly, the data indicated that the CRD was not required for Wg binding. In fact, the amount of Wg detected in wells coated with sFRP-ΔCRD (SEQ ID NO: 8) matched that seen in wells treated with full-length, epitope-tagged sFRP-1.

On the other hand, derivatives that contained the CRD domain and lacked portions of the carboxyl-terminal region showed reduced Wg binding. sFRP-Δ2 (SEQ ID NO: 6) exhibited intermediate binding activity, whereas sFRP-Δ1 (SEQ ID NO: 5) and sFRP-Δ3 (SEQ ID NO: 7) had only limited binding activity. No binding was observed in wells treated with BSA alone (data not shown). These results indicate that the carboxyl-terminal region of sFRP-1 was primarily responsible for its ability to bind Wg.

In the experiments described above, wells were coated in parallel with the same molar concentration of the various sFRP-1 derivatives, and analysis indicated that comparable amounts of each derivative adhered to the well surface. Therefore, the contrasts in relative binding efficiency were not attributable to differences in the concentration of protein coating the wells. Given the above described results, it was conceivable that the sFRP-1 derivatives could adsorb to the well surface in ways that would differentially mask a Wg binding site, however, this was shown not to be the case in subsequent binding assays performed in solution.

Wg binding in solution was tested by coating wells with native sFRP-1, Wg medium that had been preincubated for 45 minutes with varying concentrations of the sFRP-1 mutants was then added. The ability of the mutants to interact with Wg was indicated by the extent to which they could inhibit Wg binding to the wells. The results of these experiments (FIG. 3D) were in agreement with the previous pattern: sFRP-ΔCRD (SEQ ID NO: 8) competed for Wg binding as effectively as sFRP-M/H (SEQ ID NO: 4), whereas sFRP-Δ2 (SEQ ID NO: 6) had a partial effect. sFRP-Δ1 (SEQ ID NO: 5) and sFRP-Δ3 (SEQ ID NO: 7) had little or no efficacy in the competition assay. Thus, the observed differences in Wg binding to the sFRP-1 derivatives were not caused by inadvertent masking of binding sites but were due to the intrinsic properties of the derivatives.

Figure 4:
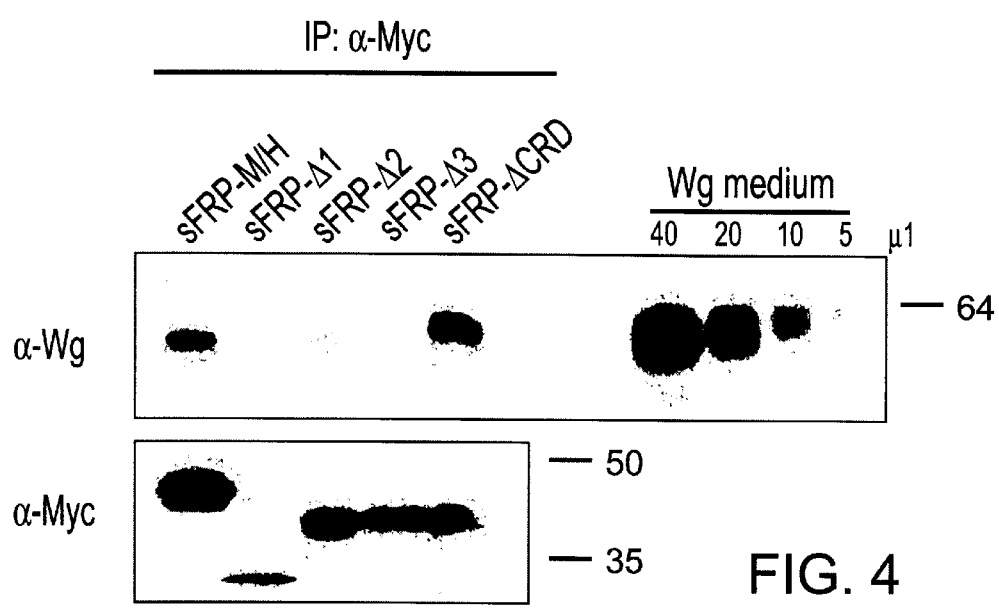
FIG. 4 is a gel showing the results of co-precipitation assays of sFRP-1 dervatives and Wg. sFRP-1 mutant proteins were incubated with Wg-containing media, precipitated with anti-Myc, and immunoblotted with anti-Wg (upper panel) or anti-Myc (lower panel). Serial dilutions of Wg medium were also analyzed. Note that sFRP-Δ1 (SEQ ID NO: 5) migrated near the bottom of the gel in the lower panel. The positions of molecular mass markers are shown at the right. IP, immunoprecipitation.

The association of sFRP-1 proteins with Wg was also examined in co-precipitation experiments. Following incubation of epitope-tagged sFRP-1 mutants with Wg medium, proteins were precipitated with anti-Myc and subsequently immuno-blotted with anti-Wg (FIG. 4). Approximately 10–20% of Wg protein was precipitated with either sFRP-ΔCRD (SEQ ID NO: 8) or sFRP-M/H (SEQ ID NO: 4). A weak association was detected with sFRP-Δ2 (SEQ ID NO: 6), but none was observed with sFRP-Δ1 (SEQ ID NO: 5) or sFRP-Δ3 (SEQ ID NO: 7). Thus, both ELISA and co-precipitation experiments showed that the CRD was not required for Wg binding.

Figure 5:
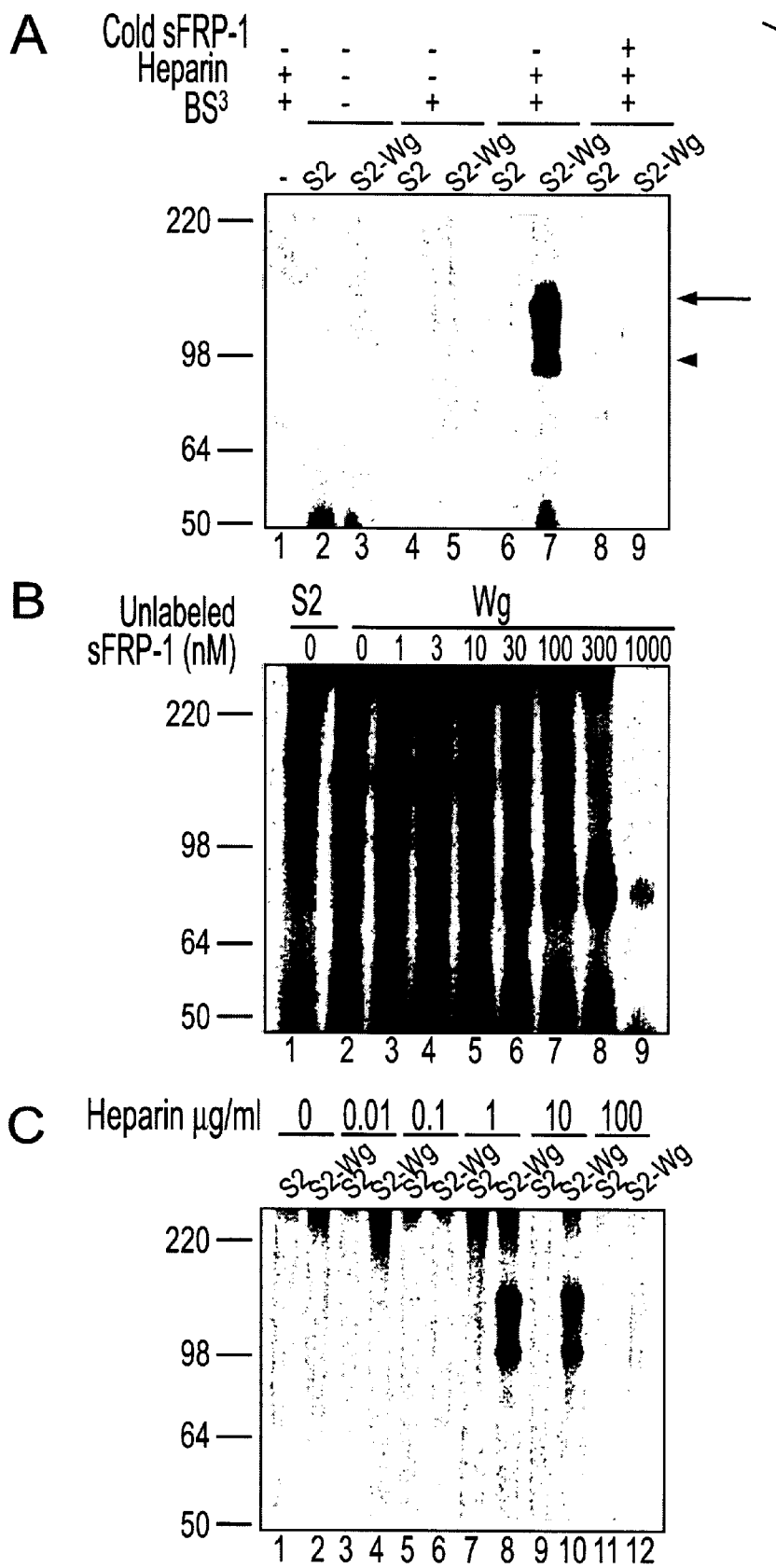
FIGS. 5A–5C include three gels showing the results from covalent cross-linking assays of sFRP-1 and Wg. FIG. A is a gel showing the results from an $^{125}$sFRP-1 incubation with medium from S2 or Wg-expressing S2 cells, followed by addition of BS 3 cross-linking agent. In some reactions, unlabeled sFRP-1 (1.7 mM) and/or heparin (10 μg/ml) were also present. Proteins immunoprecipitated with anti-Wg were separated by 8% SDS-PAGE and processed for autoradiography. Smaller and larger cross-linked complexes are indicated by arrowhead and arrow, respectively. The positions of molecular mass markers are shown at the left.

To rule out the possibility that an unidentified factor in the Wg medium might be responsible for mediating the binding interaction between sFRP-1 and Wg, covalent affinity cross-linking studies were performed with radiolabeled sFRP-1 and conditioned medium from Wg-expressing and control S2 cells. Following incubation of reactants as described under "Experimental Procedures," proteins were immuno-precipitated with anti-Wg and resolved by SDS-PAGE, and cross-linked complexes were detected by autoradiography (FIG. 5A). No complexes were observed in the absence of cross-linker or Wg. In contrast, two distinct radiolabeled bands were evident when the cross-linking reaction was carried out in the presence of Wg. The lower band had an apparent molecular mass consistent with a complex comprised of one molecule each of sFRP-1 and Wg, thereby indicating that the two proteins can interact directly with each other.

The difference in apparent size of the upper and lower bands was 35±2.9 kDa (mean±S.D., calculated from four experiments), which corresponds closely to the molecular mass of sFRP-1 (Finch et al., *Proc. Natl. Acad Sci. U.S.A.* 94:6770–6775, 1997). This suggested that the upper band is a complex containing two sFRP-1 molecules and one Wg molecule. Another possibility is that the upper band represents a ternary complex with a third unidentified partner linked to sFRP-1 and/or Wg. The absence of both bands when Wg was lacking from the cross-linking reaction, when anti-Wg immunoprecipitation was omitted, or in the presence of an excess of unlabeled sFRP-1 demonstrated that sFRP-1 and Wg were present in both complexes (FIG. 5A and data not shown). Comparable displacement of $^{125}$I-sFRP-1 by unlabeled sFRP-1 indicated that the binding affinity of tracer in the two complexes was similar (FIG. 5B). Unlabeled sFRP-ΔCRD (SEQ ID NO: 8) and sFRP-Δ2 (SEQ ID NO: 6) also competed with tracer for binding in both complexes, although neither was as potent as full-length sFRP-1.

Because sFRP-1 and Wg are both heparin-binding proteins and because heparin-sulfate proteoglycan (HSPG) had been shown to regulate Wg/Wnt activity in vivo, the role of heparin was examined in the above-described cross-linking experiment. Initial studies revealed that heparin at a concentration of 10 µg/ml caused a dramatic increase in the intensity of both bands corresponding to cross-linked complexes (FIG. 5A). Subsequently, a dose-response analysis indicated a biphasic pattern in which optimal stimulation was observed with 1–10 µg/ml of heparin (FIG. 5C). This effect was specific for heparin, because no stimulation was observed when chondroitin sulfate, keratin sulfate, or hyaluronic acid was used under similar conditions (data not shown). These data indicated that heparin and presumably HSPG have a marked impact on the interaction of sFRP-1 and Wnt proteins, as represented by Wg in this study.

Subsequent assays showed that sFRP-1 has a biphasic effect on Wg-dependent stabilization of Armadillo protein. These assays also tested the biological activity of recombinant sFRP-1 derivatives. Because Wg had been used in the binding experiments, sFRP-1 activity was examined in a Wg-dependent bioassay. As previously reported (Bhanot et al., *Nature* 382:225–230, 1996), soluble Wg increases the steady-state level of Arm in cells engineered to express DFz2 (Drosophila frizzled 2) (FIG. 6A). Inhibition of Wg/DFz2 signaling by sFRP-1 was expected, given earlier reports that sFRP-1 and other sFRP family members antagonized Wg-dependent and other Wnt-dependent duplication of the dorsal axis in early Xenopus embryos (Leyns et al., *Cell* 88:747–756, 1997; Wang et al., *Cell* 88:757–766, 1997; Rattner et al., *Proc. Natl. Acad. Sci. U.S.A.* 94:2859–2863, 1997 and Xu et al., *Development* 125:4767–4776, 1998). Indeed, high concentrations of sFRP-1 (10 and 25 mg/ml) blocked Wg activity (FIG. 6A). However, lower concentrations of sFRP-1 had the opposite effect: as little as 20 ng/ml (0.6 nM) of sFRP-1 incubated with Wg medium caused a significant increase in the amount of Arm protein relative to that observed with Wg medium alone. Maximal Arm response was seen with 100–500 ng/ml of sFRP-1. This potentiating effect was not attributable to a prolongation of the Wg half-life in solution, because Wg half-life was much longer than the duration of the assay, even in the absence of sFRP-1. sFRP-1 had no effect on Arm levels in the absence of Wg and no effect on S2 cells lacking DFz2 expression (data not shown). Thus, sFRP-1 activity presumably involved an interaction with Wg that required signaling through DFz2.

Figure 6:
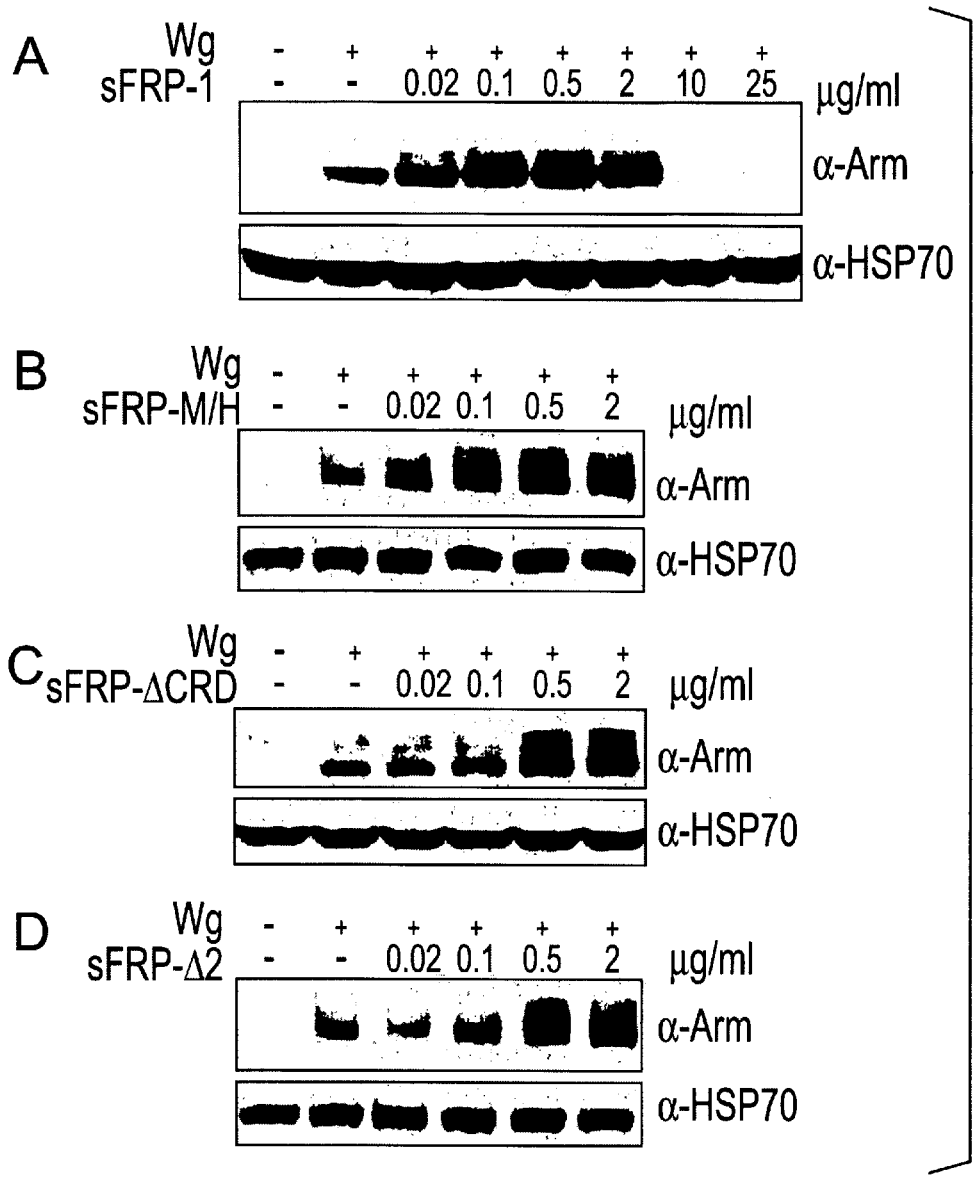
FIGS. 6A–6D include four gels showing the results from Arm stabilization assays that tested the biological activity of sFRP-1 and its derivatives.

The arm assay was also used to compare the effect of sFRP-M/H (SEQ ID NO: 4), sFRP-ΔCRD (SEQ ID NO: 8), and sFRP-Δ2 (SEQ ID NO: 6)on Wnt biological activity. sFRP-M/H (SEQ ID NO: 4) behaved like native sFRP-1 at the concentrations tested (0.02–2 mg/ml), enhancing Wg-dependent stabilization of Arm (FIG. 6B). This implied that the addition of Myc and histidine epitope tags did not alter its biological activity. sFRP-ΔCRD (SEQ ID NO: 8) and sFRP-Δ2 also increased the activity of Wg in this assay, although their potency was reduced, especially that of sFRP-Δ2 (SEQ ID NO: 6), relative to sFRP-M/H (FIG. 6, B–D). Taken together, these results demonstrated that the recombinant proteins used in the binding analysis were biologically active. This reinforced the conclusions drawn above concerning the structural requirements for Wg binding. In particular, the CRD was not required either for binding or biological activity, although its absence reduced the specific activity of sFRP-1.

B. Discussion

The present disclosure demonstrates that sFRP-1 and Wnt protein bind directly to each other. Previous reports described co-precipitation experiments in which various sFRP family members were shown to associate with one or more Wnt proteins. These results were inconclusive because, they did not address the possibility that their association might be indirect, mediated by a factor that could bind both proteins. This was a distinct possibility because neither protein was used in a purified state. In addition, some of the earlier observations were made with cells co-expressing both recombinant proteins such that association might occur during their synthesis and would not reflect a normal pattern of interaction. However, the studies described herein minimized the contribution of indirect effects by using purified preparations of sFRP-1 and an independent source of Wg. The sFRP-1/Wg binding was demonstrated both in solid phase and solution assays, utilizing ELISA and co-precipitation formats. Covalent cross-linking of $^{125}$1I-sFRP-1 with Wg provided strong evidence of a direct interaction between the two proteins. Surprisingly, besides detecting a cross-linked complex consistent in size with one sFRP-1 and one Wg molecule, a larger complex whose size suggested the presence of a second sFRP-1 molecule was also observed. Although the exact nature of this larger entity is currently unknown, taken together these results established for the first time that sFRP-1 is a direct binding partner for Wnt protein.

Additionally, the $^{125}$I-sFRP-1/Wg cross-linked complexes were detected in the absence of added heparin but were more abundant when the reaction was performed with an optimal concentration of exogenous heparin. Heparin or endogenous HSPG is believed to promote sFRP-1/Wg binding by serving as a scaffold to facilitate interaction between sFRP-1 and Wg. Alternatively, heparin/HSPG may promote binding by stabilizing a conformation of either sFRP-1 or Wg that would increase their mutual affinity or by enhancing ligand or receptor oligomerization. However, the ability to bind heparin was not itself sufficient for cross-linking to Wg; similar experiments conducted with Wg medium and a control heparin-binding polypeptide did not yield cross-linked Wg complexes (data not shown). Moreover, the spacer arm of the cross-linking agent was only 11.4 Å long, reinforcing the conclusion that sFRP-1 binds directly to Wg and presumably other Wnt proteins. Although the effect of heparin on sFRP-1/Wg binding was observed in an artificial, cell-free setting, these results are consistent with other findings suggesting an important role for HSPG in Wnt signaling in vivo. The present findings indicate that HSPG has a profound effect on Wnt activity and specifically indicate that HSPG can regulate Wnt binding interactions with sFRP proteins.

Among the most unexpected findings was the observation that the CRD was not required for Wg binding. The prevailing view that the CRD is the Wnt binding site is based on several experiments in which the Fz CRD conferred Wnt binding and/or responsiveness (Hsieh et al., *Proc. Natl. Acad. Sci. U.S.A.* 96:3546–3551, 1999; Bhanot et al., *Nature* 382:225–230, 1996; and He et al., *Science* 275:1652–1654, 1997).

Evidence that sFRP-ΔCRD (SEQ ID NO: 8) can bind Wg as shown above in multiple experimental models and was highly reproducible. The proteins were shown to interact both in a solid phase assay and in solution. sFRP-ΔCRD (SEQ ID NO: 8) also retained the full heparin-binding capacity of the native protein. Therefore, it is possible that this sFRP-1 derivative associated with Wg via soluble HSPG, whose presence in Wg-containing S2 conditioned medium had been previously inferred (Reichsman et al., *J. Cell Biol.* 135:819–827, 1996). Such a complex would not likely be detected in experiments based on the cross-linking properties of BS³; correspondingly, heparin cross-linked by BS³ to $^{125}$-sFRP-1 or a number of other heparin-binding tracer proteins (FIG. 5) was not observed. Although the details of their interaction have not been fully defined, the ability of sFRP-ΔCRD (SEQ ID NO: 8) to enhance the activity of Wg in the Arm stabilization assay distinguished it from another heparin-binding protein (data not shown) and indicated that its association with Wg has biological relevance.

The carboxyl-terminal deletion mutants that retained the CRD were remarkable for their relatively weak association with Wg. Bafico et al. (Bafico et al., *J. Biol. Chem.* 274:16180–16187, 1999), reported that a sFRP-1 truncation mutant retaining the CRD was able to coprecipitate with Wnt-1 and Wnt-2. Conversely, the experiments described above demonstrate that of all the truncation mutants, sFRP-Δ2 (SEQ ID NO: 6) exhibited an intermediate capacity to interact with Wg. This implies that sFRP-Δ2 (SEQ ID NO: 6) shares a portion of a Wnt binding epitope with sFRP-ΔCRD (SEQ ID NO: 8) or that it contains another binding site involving the CRD that was perturbed in the D1 and D3 mutants.

Previous studies involving co-expression of sFRP and Wnt proteins in the same cells indicated that sFRP family members can inhibit Wnt signaling. This was true in early Xenopus embryos because co-injection of mRNA encoding sFRP and Wnt molecules blocked Wnt-dependent duplication of the dorsal axis (Leyns et al., *Cell* 88:747–756, 1997; Wang et al., *Cell* 88:757–766, 1997; Wang et al., *J. Biol. Chem.* 271:4468–4476, 1996; Finch et al., *Proc. Natl. Acad. Sci. U.S.A.* 94:6770–6775, 1997; and Xu et al., *Development* 125:4767–4776, 1998), and in transfected cells in culture where stabilization of β-catenin was inhibited (Lin et al., *Proc. Natl. Acad. Sci. U.S.A.* 94:11196–11200, 1997 and Bafico et al., *J. Biol. Chem.* 274:16180–16187, 1999). In these instances, high local concentrations of the proteins would have been likely, corresponding to the high end of the sFRP-1 dose-response experiment in the present report that also resulted in Wnt inhibition. Surprisingly, the work described herein is the first to show that sFRP can enhance Wnt signaling under at low concentrations. Biphasic regulation by sFRP-1 provides a mechanism to facilitate the position-dependent properties of Wnt signaling; cells in close proximity to sources of sFRP-1 would be more refractory to Wnts, whereas cells at a greater distance would have their response to Wnts potentiated by a lower sFRP-1 concentration.

The molecular mechanism responsible for biphasic modulation of Wg signaling by sFRP-1 is believed to be the presence of two distinct binding sites for sFRP-1 on Wg that vary in their affinity; binding to the high affinity site promotes Wnt signaling, whereas binding to the low affinity site inhibits it. Alternatively, a higher affinity interaction of Wg with the carboxyl-terminal domain of sFRP-1 promotes signaling by presenting a favorable Wg conformation to Fz, whereas additional lower affinity binding via the CRD competes with Fz. This might involve a single sFRP-1 molecule binding to one Wg molecule, but it also could entail two sFRP-1 molecules interacting with one Wg. The cross-linking data indicates that sFRP-1 and Wg interacts with both 1:1 and 2:1 stoichiometry. Only a very small percentage of sFRP-1 tracer was detected as a homodimer in the cross-linking experiments, indicating that 2:1 stoichiometry probably is not due to binding of an sFRP-1 homodimer to Wg. Alternative mechanisms also could account for a biphasic pattern of regulation. For instance, sFRP-1/Wg might act as an agonist at low sFRP-1 concentrations, but at high concentrations sFRP-1 could interact with Fz or another cell surface component and block signaling.

Use of soluble sFRP-1 derivatives in the ELISA competition model did enable the comparison of the relative affinities of sFRP-1/Wg. The apparent affinity was in the range of 10–30 nM, rather close to the 9 nM affinity recently calculated for the interaction of XWnt8 and mFz8 (Hsieh et al., *Proc. Natl. Acad. Sci. U.S.A.* 96:3546–3551, 1999). In addition to these approximations, the Arm stabilization assays showed that recombinant sFRP-1 elicited a biological response at a subnanomolar concentration and activation was maximal at 15 nM. The higher concentrations required for inhibition of Wnt signaling might occur in restricted locations near the sites of sFRP-1 synthesis.

The results described herein establish that sFRP-1 can bind Wg and regulate Wnt signaling. It is believed that other members of the sFRP subfamily have similar properties, although much work will be required to define the specific relationships that govern the interactions of the many Wnts, sFRPs, and Fzs. Recent reports suggest that sFRP-1 has proapoptotic activity (Melkonyan et al., *Proc. Natl. Acad. Sci. U.S.A.* 94:13636–13641, 1997) and is up-regulated in certain settings following serum withdrawal (Zhou et al., *Int. J. Cancer* 78:95–99, 1998). Its chromosomal locus at 8p11–12 (Finch et al., *Proc. Natl. Acad. Sci. U.S.A.* 94:6770–6775, 1997) is a site associated with loss of heterozygosity for a variety of malignancies, and sFRP-1 expression is absent from a high percentage of human breast tumor specimens (Ugolini et al., *Oncogene* 18:1903–1910, 1999). Taken together, these observations indicate that sFRP-1 and fragments thereof function as a tumor suppressor, consistent with its ability to inhibit Wnt signaling at high concentrations.

C. Methods

Cell Culture—MDCK cells (American Type Culture Collection) were grown in Dulbecco's modified Eagle's medium (Life Technologies, Inc., Rockville, Md.) containing 10% fetal calf serum (Colorado Serum Company, Denver, Colo.) in 5% $CO_2$ at 37° C. Drosophila S2 cells and S2HSWg cells transfected with a heat shock promoter/Wg construct (Bellahcene et al., *J Bone Miner Res* 11(5):665–70, 1996 and Waltregny et al., *J Natl. Cancer Inst.* 90(13):1000–8, 1998), and S2 cells expressing DFz2 (Koeneman et al., *Prostate* 39(4):246–61, 1999) were kindly provided by the Nusse lab. All three S2 lines were cultured in Schneider's Drosophila medium (Life Technologies, Inc.) supplemented with 10% fetal calf serum, 100 units/ml penicillin, and 100 mg/ml streptomycin at 25° C. in atmospheric air. Wg-containing and S2 control media were generated as described previously (Ryden et al., *Eur. J. Biochem.* 184(2):331–6, 1989).

Immunoblotting and Immunoprecipitation—Proteins resolved by SDS-PAGE were transferred to Immobilon-P membranes (Millipore, Mass.). Unless stated otherwise, all subsequent steps were performed at room temperature. After brief washing in phosphate-buffered saline (PBS), membranes were blocked with 3% nonfat dry milk in TTBS (20 mM Tris-HCl, pH 8.0, 0.05% Tween-20, 150 mM NaCl) for 2 h. Following five washes with TTBS, membranes were incubated for 2 h with primary antibodies diluted 1:1000 (for a typical final concentration of 1–2 mg/ml) in 0.5% bovine serum albumin (BSA)/TTBS. sFRP-1 rabbit antisera were raised either against a synthetic amino-terminal peptide (Jarvis and Vedros, *Infect. Immun.* 55(1):174–80, 1987) or the full-length, purified protein. Monoclonal antibody to Wg, prepared by known techniques. Antibodies to the c-Myc and polyhistidine epitopes were from Invitrogen (Carlsbad, Calif.). After five washes with TTBS, membranes were incubated for 1 h with horseradish peroxidase conjugated to anti-mouse or anti-rabbit secondary antibodies (Amersham Pharmacia Biotech, Uppsala, Sweden) diluted 1:2000 in 0.5% BSA/TTBS. Following five more washes with TTBS, bound anti-bodies were visualized by chemiluminescence (Amersham Pharmacia Biotech) using X-Omat AR film (Kodak).

For immunoprecipitation, Wg-containing medium (80 ml) was preincubated with individual sFRP-1 derivatives (300 nM) for 10 min at room temperature. Subsequently, anti-Myc (0.2 mg) was added to the samples, which were then incubated overnight at 4° C. Sample volumes were adjusted to 500 ml with lysis buffer (50 mM HEPES, pH 7.5, 50 mM NaCl, 1% Triton X-100, 5 mM EDTA, 50 mM NaF, 6.7 mM Na4 P2O7 ,1 mM NaVO4 , 10 mg/ml aprotinin, 10 mg/ml leupeptin, 1 mM phenylmethyl-sulfonyl fluoride) and 50 ml of a 50% protein G-Sepharose slurry (Amersham Pharmacia Biotech) was added. After 1 h of incubation at 4° C. in a rotary shaker, samples were washed three times with 1 ml of lysis buffer. Final pellets were resuspended in 23×SDS sample buffer and boiled for 4 min, and the proteins were resolved by SDS-PAGE.

Expression, Purification, and Analysis of Recombinant sFRP-1 and Its Derivatives—The human sFRP-1 NotI-SmaI cDNA fragment (33) was subcloned into an XhoI site in the pcDNA3.1 expression vector (Invitrogen, Carlsbad, Calif.). To prepare derivatives containing c-Myc and polyhistidine epitopes at their carboxyl termini, cDNAs encoding full-length sFRP-1 or deletion mutants were generated by polymerase chain reaction with primers that introduced EcoRV and HindIII restriction sites at the 59 and 39 ends, respectively. The sequences comprising the various derivatives are indicated in FIG. 2A. Purified polymerase chain reaction products were ligated into the pcDNA3.1 Myc/His, C(2) expression vector (Invitrogen), and plasmid samples prepared from transformed DH5α competent cells (Life Technologies, Inc.). The fidelity of cDNAs was verified by sequence analysis.

MDCK cells ($1.5 \times 10^6$) were transfected with 10 mg of DNA of the various sFRP-1 constructs, using the calcium phosphate precipitation method. Mass cultures were selected with Geneticin (500 mg/ml) for 21 days. To isolate clonal cell lines, mass cultures were subcultured at a 1:50,000 dilution in collagen-coated wells and subsequently transferred to culture dishes for further analysis. Expression of recombinant protein was determined by immunoblotting equal quantities of total protein from conditioned medium and/or cell lysates. For large scale preparations, sFRP-1/MDCK transfectants were grown in T175 flasks until confluent. After washing with PBS, the cells were maintained in serum-free Dulbecco's modified Eagle's medium, and conditioned media were collected every 3 days for five to seven consecutive harvests. Media were clarified by centrifugation at 10,000×g for 10 min at 4° C. and filtration (pore size, 0.4 mm; Corning). Subsequently, media were concentrated 40-fold by ultrafiltration in a stirred chamber apparatus (Amicon M2000) using a Millipore YM membrane with either a 10- or 3-kDa molecular mass cut-off. Concentrated samples were snap-frozen for subsequent purification.

Native sFRP-1 was purified with HiTrap-Heparin columns (Amersham Pharmacia Biotech) equilibrated with PBS/0.3 M NaCl. After applying the sample to the column, the resin to was washed with 10 column volumes of equilibration buffer. Protein was eluted with a step gradient of increasing NaCl concentration. Aliquots from representative fractions were resolved by SDS-PAGE and analyzed by immuno-blotting or silver staining (Bio-Rad). sFRP-1 derivatives containing Myc/histidine epitopes were purified in a similar manner, only using HiTrap Chelating Affinity columns (Amersham Pharmacia Biotech). The resin (1.0 ml) was washed with 5.0 ml of water, charged with 0.5 ml of 0.1 M $NiSO_4$, and washed again with 5.0 ml of water. Following equlibration with 50 mM phosphate/10 mM imidazole buffer (pH 7.4), protein was eluted with a step gradient of increasing imidazole concentration. Selected fractions were analyzed by immunoblotting and silver staining. Typically, sFRP-1 derivatives were recovered with 0.1 M imidazole. The identity of individual sFRP-1 preparations was verified by microsequencing with an Applied Biosystems (Foster City, Calif.) protein sequencer (model 476). For sFRP-ΔCRD (SEQ ID NO: 8), 30 rounds of Edman degradation were carried out to ensure that the entire CRD was deleted.

sFRP-1/Wg ELISA Binding Assays-sFRP-1 diluted in 0.02% $NaN_3$/PBS was incubated in 96-well Falcon ELISA plates (300 ng/50 ml/well) for 2 h at 37° C. After decanting, all wells were filled with 4% BSA/0.02% $NaN_3$/PBS and incubated for an additional 2 h at 37° C. Following five washes with TAPS (0.05% Tween-20 in 0.02% $NaN_3$/PBS), 50-ml aliquots of Wg-containing or S2 control medium diluted in 1% BSA/TAPS were incubated overnight at room temperature. After five washes with TAPS, 50 ml/well of Wg mAb diluted in 1% BSA/TAPS to a final concentration of 1 mg/ml was incubated in wells for 2 h at 37° C. Another five washes in TAPS were followed by a 2 h treatment at 37° C. with 1:400 dilution of conjugated alkaline phosphatase-goat anti-mouse IgG (Sigma). After a final set of five washes with TAPS, 2 mg/ml p-nitrophenolphosphate (Sigma) in carbonate buffer (0.1 M $Na_2 CO_3$, 1 mM $MgCl_2$, pH 9.8) was added. Absorbance at 405 nm was measured with an ELISA plate reader (Bio-Rad, Hercules, Calif.). When the solid phase assay was performed with the various sFRP-1 derivatives, wells were coated with 60 nM solutions of the respective derivatives. ELISA competition experiments were performed as described above, except the indicated concentrations of sFRP-1 derivatives were preincubated with Wg conditioned medium for 45 min at room temperature prior to addition to wells that had been coated with native sFRP-1.

Covalent Cross-linking—sFRP-1 was iodinated as described previously (Kovats et al., *Science* 248(4952):220–3, 1990). Briefly, 10 mg of sFRP-1 was reacted with 1 mCi of Na 125 I in the presence of 30 mg/ml chloramine T for 30–60 s. After addition of 80 mg/ml sodium metabisulfite, the reaction mixture was applied to a heparin-Sepharose column (bed volume, 0.3 ml) equilibrated in 0.1% BSA/PBS. Labeled sFRP-1 was eluted with equilibration buffer containing 1.0 M NaCl and stored in frozen aliquots. Approximately 50 ml of Wg-containing or control medium was incubated with 1 mCi of $^{125}$I-sFRP-1 for 40 min at room temperature. In some experiments, varying concentrations of heparin (12 kDa from porcine intestine; Fisher, Madison, Wis.) or unlabeled sFRP-1 were also present (see FIGS. for details). After addition of 1 mM bis(sulfosuccinimidyl) suberate ($BS^3$) cross-linking agent (Pierce, Rockford, Ill.), the incubation continued for 20 min. The reaction was quenched with 20 mM glycine/1 mM Tris-HCl, and the mixture was incubated with Wg mAb (10 mg/ml) overnight at 4° C. After addition of 0.5 ml of lysis buffer and 50 ml of a 50% protein G-Sepharose slurry, samples were incubated for 1 h at 4° C. Beads were pelleted by centrifugation at 1000×g for 3 min at 4° C. and washed three times with 1 ml of lysis buffer. The final pellets were resuspended in 2×SDS sample buffer, boiled for 4 min, and briefly microfuged to facilitate transfer. Protein samples were resolved in 8% polyacrylamide gels by SDS-PAGE. After fixation in 20% methanol/10% acetic acid for 45 min, the gel was dried and exposed to X-Omat AR film (Kodak) for autoradiography.

Armadillo Stabilization Assay—This assay was performed as described previously (Ryden et al., *Eur J Biochem* 184(2):331–336, 1989). The blots were probed with two primary antibodies, mouse monoclonal anti-Arm antibody N27A at 1:50 and mouse monoclonal anti-HSP70 at 1:200,000 and one secondary antibody, goat anti-mouse IgG conjugated to horseradish peroxidase (Bio-Rad). Immunoreactive protein bands were visualized by treating the blots with ECL reagents (Amersham Pharmacia Biotech) and then exposing them to x-ray film. Equal loading of total protein was confirmed by inspection of the HSP70 protein band in each sample lane.

EXAMPLES

Example 1

Expression and Purification of sFRP Fragments and Variants Thereof sFRP fragments and variants thereof may be purified from the MDCK cells ($1.5 \times 10^6$; ATCC NO. CCL-34) that were transfected with sFRP encoding vectors as described above. sFRP fragments and variants thereof may also be purified from a tissue source using conventional biochemical techniques, or produced recombinantly in either prokaryotic or eukaryotic cells using methods well-known in the art (for example, those described in Sambrook et at., *Molecular Cloning. A Laboratory Manual,* Cold Spring Harbor, N.Y., 1989). The recombinant expression of sFRP fragments is described in (Uren et al., *Journal of Biological Chem.* 275:4374–4382, 2000). Furthermore, the nucleic acid sequences encoding sFRP are available on GenBank, and include the cDNA sequence shown in SEQ. ID NO: 1.

Recombinant sFRP fragments and variants thereof may be conveniently obtained using commercial systems designed for optimal expression and purification of fusion proteins. Such fusion proteins typically include a protein tag that facilitates purification. Examples of such systems include: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). For example, the pMAL expression system utilizes a vector that adds a maltose binding protein to the expressed protein. The fusion protein is expressed in *E. coli.* and the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column. Eukaryotic expression systems may also be employed, including Pichia, tobacco and Baculovirus expression systems, such as those available commercially from Invitrogen.

For each of these systems, the entire sFRP protein may be produced by ligating the open reading frame (ORF) of sFRP into the vector. To ensure effective expression, the ORF must be operably linked to the vector, i.e., must be joined such that the reading frame of the ORF is aligned with the reading frame of the protein tag. Where fragments of sFRP are to be expressed, an ORF encoding the desired fragment may be amplified by polymerase chain reaction (PCR) from the sFRP cDNA, cloned, purified and then ligated into the expression vector. Alternatively, the amplified fragment may be ligated directly into the expression vector. It may also be possible, depending on the availability of suitable restriction sites in the sFRP cDNA to obtain the desired fragment by appropriate restriction endonuclease digestion, such that it can be directly cloned into the expression vector.

Purification of the expressed protein can be achieved either using the purification regimen appropriate for the expression tag (if a commercial expression/purification system is used), or conventional affinity chromatography using antibodies, preferably monoclonal antibodies, that recognize the appropriate regions of sFRP may be employed.

Where sFRP fragments are to be used, such fragments may alternatively be generated through digestion of the full-length sFRP protein with various proteases. The fragments may then be separated based on their unique size, charge or other characteristics. sFRP fragments may also be synthetically generated through the use of known peptide synthesis methods.

Example 2

Methods of Developing Screening Assays for Molecules that Modulate Wnt Protein Activity In light of the present disclosure, one of ordinary skill in the art is enabled to practice new screening methodologies that are useful for the identification of proteins and other compounds which bind to, or otherwise directly interact with, the complex formed by sFRP or fragments thereof and Wnt (sFRP/Wnt). The proteins and compounds include endogenous cellular components which disrupt the binding of sFRP/Wnt. Thus, in one series of embodiments, cell lysates or tissue homogenates may be screened for proteins or other compounds that disrupt sFRP/Wnt binding. Alternatively, any of a variety of exogenous compounds, both naturally occurring and/or synthetic (e.g., libraries of small molecules or peptides), may be screened for the ability to disrupt sFRP/Wnt. Small molecules are particularly preferred in this context because they are more readily absorbed after oral administration, have fewer potential antigenic determinants, and/or are more likely to cross the blood brain barrier than larger molecules such as nucleic acids or proteins.

Furthermore, the identification of deletion mutants (i.e., sFRP-ΔCRD, SEQ ID NO: 8) that are significantly smaller than full length sFRP but yet maintain the ability to bind to and regulate Wnt activity can serve as "lead compounds" in the design and development of new pharmaceuticals. For example, as is well known in the art, sequential modification of small molecules (e.g., amino acid residue replacement with peptides; functional group replacement with peptide or non-peptide compounds) is a standard approach in the pharmaceutical industry for the development of new pharmaceuticals. Such development generally proceeds from a "lead compound" which is shown to have at least some of the activity (e.g., low concentrations of sFRP-ΔCRD (SEQ ID NO: 8) increases Wnt activity) of the desired pharmaceutical. In particular, when one or more compounds having at least some activity of interest (e.g., modulation of Wnt activity) are identified, structural comparison of the molecules can greatly inform the skilled practitioner by suggesting portions of the lead compounds which should be conserved and portions which may be varied in the design of new candidate compounds. Thus, the present invention also provides potential lead compounds as well as means of identifying such lead compounds which may be sequentially modified to produce new candidate compounds for use in the treatment of diseases associated with abnormal Wnt activity, i.e., cancer. These new compounds then may be tested both for Wnt-binding or blocking (e.g., in the binding assays described above) and for biological efficacy (e.g., in the Arm assay described herein). This procedure may be iterated until compounds having the desired therapeutic activity and/or efficacy are identified.

The effect of agents that disrupt sFRP/Wnt binding can be monitored using the Arm assay described above. Agents that disrupt sFRP/Wnt binding and enhance Wnt signaling are useful for treating conditions associated with decreased Wnt activity and agents that are found to disrupt sFRP/Wnt binding and increase Wnt activity are useful for treating diseases associated with increased Wnt activity such as neoplasia development. Methods of detecting such binding include the cross-linking assay described above as well as other methods that involve monitoring changes in fluorescence, molecular weight, or the concentration of either Wnt or sFRP, either in a soluble phase or in a substrate-bound phase.

Once identified by the methods described above, the candidate compounds may then be produced in quantities sufficient for pharmaceutical administration or testing (e.g., .mu.g or mg or greater quantities), and formulated in a pharmaceutically acceptable carrier (see, e.g., Remington's Pharmaceutical Sciences, Gennaro, A., ed., Mack Pub., 1990). These candidate compounds may then be administered to the transformed cells of the invention, to the transgenic animal models of the invention, to cell lines derived from the animal models or from human patients.

The proteins or other compounds identified by these methods may be purified and characterized by any of the standard methods known in the art. Proteins may, for example, be purified and separated using electrophoretic (e.g., SDS-PAGE, 2D PAGE) or chromatographic (e.g., HPLC) techniques and may then be microsequenced. For proteins with a blocked N-terminus, cleavage (e.g., by CNBr and/or trypsin) of the particular binding protein is used to release peptide fragments. Further purification/characterization by HPLC and microsequencing and/or mass spectrometry by conventional methods provides internal sequence data on such blocked proteins. For non-protein compounds, standard organic chemical analysis techniques (e.g., IR, NMR and mass spectrometry; functional group analysis; X-ray crystallography) may be employed to determine their structure and identity.

Methods for screening cellular lysates, tissue homogenates, or small molecule libraries for candidate sFRP/Wnt disrupting molecules are well known in the art and, in light of the present disclosure, may now be employed to identify compounds which disrupt such binding and increase or decrease Wnt biological activity.

In light of the present disclosure, a variety of affinity binding techniques well known in the art may be employed to isolate proteins (i.e. lead compounds) or other compounds which disrupt sFRP/Wnt binding. In general, sFRP or a fragment thereof can be immobilized on a substrate (e.g., a column or filter) and a solution containing Wnt protein can be introduced to the column to allow formation of the sFRP/Wnt complex. Then a solution including the test compound(s) is introduced to the column under conditions which are permissive for binding. The substrate is then washed with a solution to remove unbound or weakly bound molecules. A second wash may then elute those compounds which strongly bound to the immobilized sFRP. Alternatively, the test compounds may be immobilized and a solution containing sFRP/Wnt may be contacted with the column, filter or other substrate. The ability of either the sFRP or fragment thereof, or the Wnt protein to bind to the test compound may be determined as above.

In other embodiments the invention provides for methods of identifying compounds with the ability to modulate the activity of Wnt proteins. Furthermore, the identification of the biphasic nature of sFRP/Wnt interactions allows for the development of compounds that can specifically modulate increases and decreases in Wnt biological activity. Using the Arm assay described above modifications in the sFRP protein and fragments thereof can be sequentially made. These modified proteins can then be tested for their ability to increase Wnt activity. In other words the discovery that sFRP and fragments thereof can cause an increase of Wnt activity can be exploited to identify sFRP mutants with enhance Wnt inducing activity.

Example 3

Assessing sFRP and Fragments Thereof for Their Ability to Modulate Wnt Biological Activity Following the purification of sFRP or a fragment of sFRP, the biological activity can be assessed using the methods described above. Specifically, the Arm assay can be used to determine the ability of the sFRP fragment or variant thereof to modulate Wnt activity. Similarly, an assay for β-catenin showing biochemical response to Wnts can be also used to monitor Wnt biological activity (Papkoff et al., *Mol. Cell Biol.* 16:2128–2134, 1996; and Shimizu et al. *Cell Growth and Diff* 8:1349–1358, 1997, which are herein incorporated by reference). Finally, the ability of sFRP binding fragments and mimetics thereof to bind to Wnt and modulate its activity can be tested using the cross-linking assays described above.

Example 4

Sequence Variants

While the amino acid sequence of the prototypical human sFRP protein is provided in SEQ. ID NO: 3, and the sequence of a cDNA molecule encoding this protein is given in SEQ. ID NO: 2, one of skill in the art will appreciate that the practice of this invention is not limited to these precise sequences. Thus, the invention may be practiced with molecules that differ from the exact molecules disclosed, but which retain the requisite biological activity.

Furthermore, variants of sFRP fragments that have been modified such that they bind to Wnt proteins but do not contain the CRD region of particular interest. These variants will retain the ability to specifically bind Wnt proteins.

As mentioned above, the fragments and variants of sFRP described supra, are characterized by their ability to modulate Wnt biological activity. This ability, however, is concentration dependant and a low concentration of sFRP fragments may serve to enhance Wnt activity and at high concentrations it may serve to suppress Wnt activity. When sFRP fragments and variants thereof are used to suppress Wnt activity, they can be used to modulate conditions associated with increased Wnt activity such as tumor growth. When used to inhibit tumor growth a given sFRP fragment, such as the sFRP-1-ΔCRD fragment (SEQ ID NO:8), will be found to be biologically active if it causes at least 30% inhibition of tumor growth when compared to a non-treated control. However, it is likely that some therapeutically active fragments and variants of sFRP will show an increased level of Wnt inhibition. For example, some variants and fragments of sFRP will show at least 40% inhibition, at least 50% inhibition, at least 60% inhibition, or at least 70% inhibition. Similarly, the biphasic nature of sFRP and fragments thereof means that these polypeptides can be used to increase Wnt activity. Moreover, using the ARM assays described above it is now possible to individually assess the biological activity of a given variant or fragment of sFRP, and to determine if it can cause and increase or a decrease in Wnt activity.

The therapeutically effective fragments and variants of sFRP are also characterized by the number of amino acid residues that they contain. For example, in some instances it may be desirable to use relatively short fragments and variants of sFRP. These short fragments and variants of sFRP may contain at least 5, 10, 20, or 30 contiguous amino acids residues of the sFRP sequence. However, such short fragments and variants of sFRP will maintain the ability to bind Wnt proteins.

Additionally, it is possible to vary the cDNA sequences encoding therapeutically effective fragments or variants of sFRP while still encoding a protein having the desired biological activity. In their simplest form, such sequence variants may differ from the disclosed sequences by alteration of the coding region to fit the codon usage bias of the particular organism into which the molecule is to be introduced. Additionally, the coding region may be altered by taking advantage of the degeneracy of the genetic code to alter the coding sequence in such a way that, while the nucleotide sequence is substantially altered, it nevertheless encodes a protein having an amino acid sequence identical or substantially similar to the disclosed sFRP protein sequence. For example, the seventh amino acid residue of the sFRP-1-ΔCRD fragment (SEQ ID NO: 8) is Glu, (E). This is encoded in the sFRP-1-ΔCRD open reading frame (ORF) by the nucleotide codon triplet GAG. Because of the degeneracy of the genetic code, one other nucleotide codon, GAA, also encodes for glutamic acid. Thus, the nucleotide sequence of the sFRP-1-ΔCRD ORF could be changed at this position to GAA without affecting the amino acid composition of the encoded protein or the characteristics of the protein.

As previously mentioned, the invention may also be practiced with sFRP fragments that vary in amino acid sequence from the sequence shown in SEQ. ID NO: 3. These variants include proteins that differ in amino acid sequence from the disclosed sequence but which retain the ability to bind Wnt proteins. Such proteins may be produced by manipulating the nucleotide sequence of ORF that encodes the protein, for example by site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein.

Conservative substitutions replace one amino acid with another amino acid that is similar in size, hydrophobicity, etc. Such substitutions generally are conservative when it is desired to finely modulate the characteristics of the protein. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

More substantial changes in function or other features may be obtained by selecting substitutions that are less conservative than those described above, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed through the use of the biological assays described above.

Example 5

Use of sFRP-1 to Increase Wnt Activity

Transgenic mice that have had specific Wnt genes deleted (knockout mice) display specific developmental disorders, such as Wnt-4 knockout mice which fail to develop kidneys and female organs, and Wnt-7a knockout mice which display defects in limb development (Stark et al., Nature 372:679–683, 1994; Vainio et al., Nature 397:405–409, 1999; Parr et al., Nature 374:350–353, 1995). Consistent with the above references Wnt expression has been observed to fluctuate during the estrous cycle (Miller et al., *Mech. Of Development* 76:91–99, 1998). Hence, sFRP and fragments thereof are believed to be useful for increasing Wnt activity in conditions that are characterized by developmental disorders, such as renal agenesis.

Example 6

Incorporation of Therapeutically Effective Fragments and Variants of sFRP into Pharmaceutical Compositions For administration to animals, purified sFRP fragments or variants thereof are generally combined with a pharmaceutically acceptable carrier. Pharmaceutical preparations may contain only a single sFRP fragment, or may be composed of more than one variety of sFRP fragments. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, human albumin or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As is known in the art, protein-based pharmaceuticals may be only inefficiently delivered through ingestion. However, pill-based forms of pharmaceutical proteins may be alternatively be administered subcutaneously, particularly if formulated in a slow-release composition. Slow-release formulations may be produced by combining the target protein with a biocompatible matrix, such as cholesterol. Another possible method of administering protein pharmaceuticals is through the use of mini osmotic pumps. As stated above a biocompatible carrier would also be used in conjunction with this method of delivery.

It is also contemplated that sFRP fragments could be delivered to cells in the nucleic acid form and subsequently translated by the host cell. This could be done, for example through the use of viral vectors or liposomes. Liposomes could also be used for the delivery of the protein itself.

The pharmaceutical compositions of the present invention may be administered by any means that achieve their intended purpose. Amounts and regimens for the administration of sFRP fragments can be determined readily by those with ordinary skill in the clinical art of treating conditions associated with abnormal Wnt activity. For use in treating these conditions, the described proteins are administered in an amount effective to either increase Wnt biological activity or decrease Wnt biological activity. Doses sufficient to achieve a tissue concentration that causes an increase or a decrease in Wnt biological activity may be determined by using the amounts described in the forgoing examples. The peptides or proteins may be administered to a host in vivo, such as for example, through systemic administration, such as intravenous or intraperitoneal administration. Also, the peptides or proteins may be administered intralesionally: i.e. the peptide or protein is injected directly into the tumor or affected area.

Effective doses of sFRP fragments for therapeutic application will vary depending on the nature and severity of the condition to be treated, the age and condition of the subject and other clinical factors. Thus, the final determination of the appropriate treatment regimen will be made by the attending clinician. Typically, the dose range will be from about 0.1 µg/kg body weight to about 100 mg/kg body weight. Other suitable ranges include doses of from about 1 µg/kg to 10 mg/kg body weight. The dosing schedule may vary from once a week to daily depending on a number of clinical factors, such as the subject's sensitivity to the protein. Examples of dosing schedules are 3 µg/kg administered twice a week, three times a week or daily; a dose of 7 µg/kg twice a week, three times a week or daily; a dose of 10 µg/kg twice a week, three times a week or id daily; or a dose of 30 µg/kg twice a week, three times a week or daily. In the case of a more aggressive disease it may be preferable to administer doses such as those described above by alternate routes including intravenously or intrathecally. Continuous infusion may also be appropriate.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

We claim:

1. An isolated polypeptide, comprising an amino acid sequence at least 90% homologous to the amino acid sequence set forth as SEQ ID NO: 8, wherein the polypeptide comprises a deletion of a cysteine rich domain that stretches from amino acid 57 through amino acid 165 of the amino acid sequence as set forth as SEQ ID NO: 3, and wherein the polypeptide binds to wingless protein.

2. The isolated polypeptide according to claim 1, comprising the amino acid sequence set forth as SEQ ID NO: 8.

3. An isolated protein consisting of an amino acid sequence set forth as SEQ ID NO: 8, wherein the protein binds to wingless protein.

4. A composition comprising a polypeptide according to claim 1, and a pharmaceutically acceptable carrier.

5. The isolated polypeptide of claim 1, wherein the isolated polypeptide comprises an amino acid sequence at least 95% homologous to the amino acid sequence set forth as SEQ ID NO: 8.

6. A fusion protein comprising an expression tag fused to the polypeptide of claim 1.

7. The isolated polypeptide of claim 1, wherein the isolated polypeptide comprises an amino acid sequence at least 98% homologous to the amino acid sequence set forth as SEQ ID NO: 8.

8. A composition comprising the polypeptide of claim 2 in a pharmaceutically acceptable carrier.

9. The isolated polypeptide of claim 1, wherein the isolated polypeptide stabilizes Armadillo protein.

* * * * *

UNITED STATES PATENT AND TRADEMARK OFFICE
CERTIFICATE OF CORRECTION

PATENT NO.        : 6,600,018 B1
APPLICATION NO. : 09/546043
DATED             : July 29, 2003
INVENTOR(S)       : Rubin et al.

It is certified that error appears in the above-identified patent and that said Letters Patent is hereby corrected as shown below:

Column 2, line 24, "with least" should read --with at least--.

Column 3, line 38, "dervatives" should read --derivatives--.

Column 3, line 48, "$^{125}$sFRP-1" should read --$^{125}$I-sFRP-1--.

Column 3, line 57, "is gel" should read --is a gel--.

Column 8, line 45, "secreted. and" should read --secreted and--.

Column 11, line 27, "6)on" should read --6) on--.

Column 13, line 19, "signaling under at low" should read --signaling at low--.

Column 14, line 60, "Na4 P2O7 , 1 mM NaV04 , 10" should read --$Na_4P_2O_7$, 1 mM $NaVO_4$, 10--.

Column 17, line 13, "et at.," should read --et al.,--.

Column 17, line 14, "*Cloning.*" should read --*Cloning*:--.

Column 19, line 67, "enhance" should read --enhanced--.

Column 20, line 37, "dependant" should read --dependent--.

Column 20, line 65, "acids residues" should read --acid residues--.

Column 22, lines 48-49, "may be alternatively" should read --may alternatively--.

Column 23, line 6, "forgoing" should read --foregoing--.

UNITED STATES PATENT AND TRADEMARK OFFICE
CERTIFICATE OF CORRECTION

PATENT NO. : 6,600,018 B1
APPLICATION NO. : 09/546043
DATED : July 29, 2003
INVENTOR(S) : Rubin et al.

It is certified that error appears in the above-identified patent and that said Letters Patent is hereby corrected as shown below:

Column 24, line 8, "id daily," should read --daily;--.

Signed and Sealed this

Sixth Day of October, 2009

David J. Kappos
*Director of the United States Patent and Trademark Office*